United States Patent
Rkyek et al.

(10) Patent No.: US 8,420,812 B2
(45) Date of Patent: Apr. 16, 2013

(54) PROCESS FOR THE PALLADIUM-CATALYZED COUPLING OF TERMINAL ALKYNES WITH HETEROARYL TOSYLATES AND HETEROARYL BENZENESULFONATES

(75) Inventors: Omar Rkyek, Kassel (DE); Marc Nazare, Frankfurt am Main (DE); Andreas Lindenschmidt, Frankfurt am Main (DE); Jorge Alonso, Mannheim (DE); Matthias Urmann, Frankfurt am Main (DE); Nis Halland, Frankfurt am Main (DE)

(73) Assignee: Sanofi, Paris (FR)

( * ) Notice: Subject to any disclaimer, the term of this patent is extended or adjusted under 35 U.S.C. 154(b) by 344 days.

(21) Appl. No.: 12/645,508

(22) Filed: Dec. 23, 2009

(65) Prior Publication Data

US 2010/0261900 A1    Oct. 14, 2010

Related U.S. Application Data

(63) Continuation of application No. PCT/EP2008/004928, filed on Jun. 19, 2008.

(30) Foreign Application Priority Data

Jul. 3, 2007 (EP) .................................. 07290839.5

(51) Int. Cl.
*C07D 213/127* (2006.01)
*C07D 213/26* (2006.01)
*C07D 215/12* (2006.01)
*C07D 239/26* (2006.01)

(52) U.S. Cl.
USPC ........... 544/242; 544/335; 546/118; 546/119; 546/152; 546/176; 546/342; 546/346; 546/350; 546/352; 548/361.1; 548/373.1; 548/375.1; 548/377.1; 549/61; 549/71

(58) Field of Classification Search .................. 544/242, 544/335; 546/118, 119, 152, 176, 342, 346, 546/350, 352; 548/361.1, 373.1, 375.1, 377.1; 549/61, 71
See application file for complete search history.

(56) References Cited

PUBLICATIONS

Benderitter et al., 2-Amino-6-iodo-4-tosyloxypyrimidine: a versatile key intermediate for regioselective functionalization of 2-aminopyrimidines in 4- and 6-positions, Tetrahedron, 63(50), pp. 12465-12470 (Aug. 2007).*
Li et al., Synthesis of a Diverse Series of Phosphocoumarins with Biological Activity, Organic Letters, 7(22), pp. 4919-4922 (2005).*
Rollet et al., Copper-free heterogeneous catalysts for the Sonogashira cross-coupling reaction: Preparation, characterisation, activity and applications for organic synthesis, Journal of Molecular Catalysis A: Chemical, 241(1-2), pp. 39-51 (2005).*
Wu et al., Synthesis of 4-substituted Coumarins via the Palladium-catalyzed cross-couplings of 4-tosylcoumarins with terminal acetylenes and organozinc reagents, Journal of Organic Chemistry, 66(10), pp. 3642-3645 (2001).*
Djakovitch, Lauren, et al., "Sonogashira cross-coupling reactions catalyzed by copper-free palladium zeolites", Advanced Synthesis & Catalysis, 346(13-15), 1782-1792 Coden: ASCAF7; ISSN: 1615-4150, 2004, XP002460668.
Numata, A., et al., "General synthetic method for naphthyridines and their N-oxides containing isoquinolinic nitrogen", Synthesis 1999 Germany, No. 2, 1999, pp. 306-311, XP002460669; ISSN: 0039-7881.
Boukouvalas et al., "Facile access to 4-(1-alkynyl)-2(5H)-furanones by Sonogashira coupling of terminal acetylenes wth beta-tetronic acid bromide: efficient synthesis of cleviolide", Tetrahedron Letters, Elsevier, Amsterdam, NL, vol. 48, No. 1, Nov. 30, 2006, pp. 105-107, XP005785961; ISSN: 0040-4039.
Novak, Z. et al, "Sonogashira coupling of aryl halides catalyzed by palladium on charcoal", Journal of Organic Chemistry, Apr. 18, 2003 United States, vol. 68, No. 8, pp. 3327-3327, XP002460686; ISSN: 0022-3263.
Gelman, D. et al., "Efficient palladium-catalyzed coupling of aryl chlorides and tosylates with terminal alkynes: use of a copper cocatalyst inhibits the reaction", Angewandte Chemie. International Edition, Wiley VCH Verlang, Weinheim, DE, vol. 42, 2003, pp. 5993-5993, XP002387107; ISSN: 1433-7851.

* cited by examiner

*Primary Examiner* — Deepak Rao
(74) *Attorney, Agent, or Firm* — Scully, Scott, Murphy & Presser, P.C.

(57) ABSTRACT

A process for the palladium-catalyzed coupling of terminal alkynes with heteroaryl tosylates and heteroaryl benzenesulfonates
The present invention relates to a process for the regioselective synthesis of compounds of the formula (I),

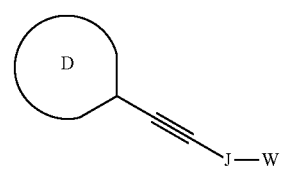

(I)

wherein D, J and W have the meanings indicated in the claims. The present invention provides an efficient and general palladium-catalyzed coupling process of heteroaryl tosylates with terminal alkynes to a wide variety of substituted, multifunctional heteroaryl-1-alkynes of the formula I.

15 Claims, No Drawings

PROCESS FOR THE PALLADIUM-CATALYZED COUPLING OF TERMINAL ALKYNES WITH HETEROARYL TOSYLATES AND HETEROARYL BENZENESULFONATES

FIELD OF THE INVENTION

The present invention relates to a process for the regioselective synthesis of compounds of the formula (I),

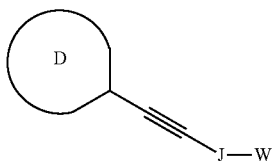

wherein D, J and W have the meanings indicated below and which are useful as intermediates for the preparation of valuable pharmaceutically active ingredients.

BACKGROUND OF THE INVENTION

The present invention relates to an efficient and general palladium-catalyzed, regioselective process for the preparation of a wide variety, of multifunctionally substituted aromatic heteroaryl-1-alkynes of the formula (I) starting from aromatic heteroaryl tosylates and terminal alkynes.

Heteroaryl-1-alkynes play an important role as key synthetic intermediates. The ability of the alkyne moiety of intermediates of the formula I to selectively react with various electrophiles or nucleophiles with or without catalytic assistance of acids or bases or transition metal is well known to those skilled in the art. Thus, heteroaryl-1-alkynes are valuable synthetic precursors for a wide variety of other compound classes, like for example heteroaromatic analogues of indoles, benzofuranes, benzothiophenes, isoquinolines, N-oxide isoquinolines, acetophenones, benzoic acids, heteroaryl-alkenyls, naphthalenes, cinnolines, chromenones and isocoumarins. In addition, heteroaryl-1-alkynes are well known as pharmaceutically active ingredients and several reports document the activity on a variety of biological targets, as well as the fact that several heteroaryl-1-alkynes are in development or are marketed as drugs (J B. G. Czito, T. J. Hong, D. P. Cohen, W. P. Petros, D. S. Tyler, T. N. Pappas, D. L. Yu, C. G. Lee, A. C. Lockhart, M. A. Morse, N. Fernando, H. I. Hurwitz, Cancer Invest. 2006, 24, 9-17; J. J. Reid, Curr. Opin. Invest. Drugs 2001, 2, 68-71, Y. Iso, E. Grajkowska, J. T. Wroblewski, J. Davis, N. E. Goeders, K. M. Johnson, S. Sanker, B. L. Roth, W. Tueckmantel, A. P. Kozikowski, J. Med. Chem. 2006, 49, 1080-1100.) The use of heteroaryl-1-alkynes is of course not limited to the above-mentioned pharmaceutical application. For example it is well known that heteroaryl-1-alkynes can be useful in agricultural applications like for example as herbicides, fungicides, nematicidals, parasiticides, insecticides, acaricides and arthropodicides. In addition they are used as diagnostic agents, liquid crystals and in polymers.

Among the synthetic repertoire for the preparation of heteroaryl-1-alkynes, the transition metal catalyzed formation of the C(sp)-C(sp$^2$) bond between the heteroaryl and the alkyne moiety is by far the most commonly used strategy. For this purpose numerous transition metal catalyzed cross-coupling methodologies between a heteroaryl halide or heteroaryl triflate and an organometalic alkyne involving for example discrete zinc, tin, boron, copper, and silicon species have been developed. In contrast to these methods the palladium-catalyzed and optionally copper co-catalyzed cross-coupling of an heteroaryl halide or heteroaryl triflate and a non-metalated terminal alkyne as precursors ("Sonogashira coupling") has turned out to be one of the most powerful and straightforward methods for the construction of heteroaryl-1-alkynes, since terminal alkynes can be used without prior transformation into an organometalic derivative.

Despite the large number of applications of the Sonogashira reaction, the coupling partners of the alkyne component are heteroaryl iodides, heteroaryl bromides and more recently also heteroaryl chlorides and heteroaryl triflates. All described Sonogashira couplings involving tosylates are limited to non-aromatic imino-tosylates or enol-tosylates (P. Jones et al. Tetrahedron 2002, 58, 9973-9981; X. Li et al. Org. Lett. 2005, 7, 4919-4922; J. Wu et al. J. Org. Chem. 2001, 66, 3642). A further Sonogashira coupling reaction with the non-aromatic 4-tosyl-6-methyl-2H-pyran-2-one catalyzed by a zeolite supported, heterogenous palladium-catalyst was disclosed by L. Djakovitch and P. Rollet (Adv. Synth. Catal.; 2004, 346, 1782-1792).

It has now been found that aromatic heteroaryl-1-alkynes of the formula I can be prepared using heteroaryl-tosylates. The object is achieved by a homogenous palladium catalyzed Sonogashira reaction using aromatic heteroaryl-tosylates and terminal alkynes in the presence of a base, a ligand and a protic solvent.

The use of heteroaryl tosylates or heteroaryl benzensulfonate derivatives offers various advantages over the use of heteroaryl triflates or heteroaryl nonaflates. They are easily prepared by reacting the corresponding phenol with Tos$_2$O or TosCl, which are stable, inexpensive, and easy to handle solid reagents on large scale, in comparison to the highly reactive, moisture sensitive and expensive Tf$_2$O or TfCl, required for the preparation of the heteroaryl triflates. Furthermore, the resulting heteroaryl tosylates are often highly crystalline solids simplifying subsequent purification procedures. Moreover heteroaryl tosylates are less reactive than heteroaryl triflates and are therefore less prone to unwanted hydrolytic cleavage by water or other protic solvents. The superior stability enables those substrates to remain unaffected by various reaction conditions allowing for example to introduce the tosylate group at an early stage of a synthesis and to carry the tosyl moiety unaffected through various other synthetic transformations and then finally to react the heteroaryl tosylate group in a Sonogashira cross coupling reaction.

SUMMARY OF THE INVENTION

The present invention provides an efficient and homogenous palladium-catalyzed coupling process for aromatic heteroaryl tosylates of the formula II with terminal alkynes of the formula III to prepare aromatic heteroaryl-1-alkynes of formula I and thus provides a new synthetic route with a good time- and cost effectiveness. The advantages of the present invention is a process for the preparation of compounds of formula I under catalytic, mild and general reaction condition for the synthesis of substituted heteroaryl-1-alkynes. The heteroaryl tosylates of the formula II are easily and inexpensively obtainable from the corresponding phenols and are stable and often crystalline solids, conveniently to purify intermediates. Thus, the process is very time- and cost-effective. Moreover the reaction conditions are compatible with a broad range of functional groups and a large variety of starting materials, which are easily accessible or even commercially available.

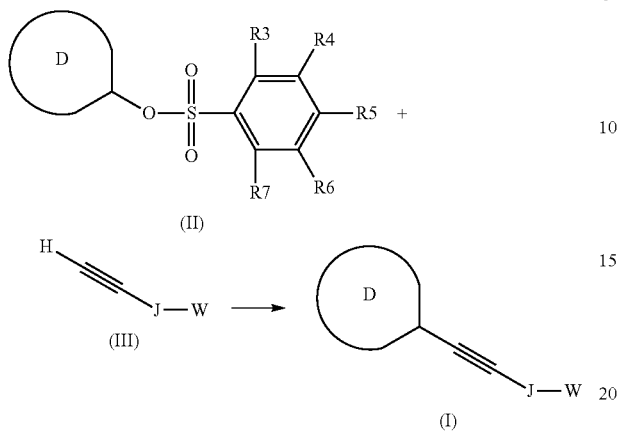

DETAILED DESCRIPTION OF THE INVENTION

The invention therefore relates to a process for preparing a compound of formula I

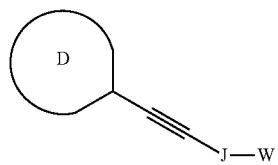

and/or all stereoisomeric forms of the compound of formula I, and/or mixtures of these forms in any ratio, and/or a physiologically tolerated salt of the compound of formula I, wherein D is a $(C_4-C_{14})$-heteroaryl ring system, which is a 4- to 14-membered aromatic cyclic residue, which consists depending on the number of ring atoms out of one, two or three ring systems, wherein one or more of the 4 to 14 ring carbon atoms are replaced by heteroatoms such as nitrogen, oxygen or sulfur, wherein heteroaryl is unsubstituted or mono-, di-, tri- four- or five times substituted independently of one another by R1, J is a covalent bond,
—$(C_1-C_6)$-alkylene, wherein alkylene is unsubstituted or mono-, di- or trisubstituted independently of one another by R2,
—$(C_3-C_8)$-cycloalkyl, wherein cycloalkyl is unsubstituted or mono-, di- or trisubstituted independently of one another by R14,
—$(C_6-C_{14})$-aryl, wherein aryl is unsubstituted or mono-, di-, tri- or four times substituted independently of one another by R13, or
—$(C_4-C_{14})$-heteroaryl ring system, which is as defined above, wherein heteroaryl is unsubstituted or mono-, di-, tri- or four times substituted independently of one another by R13, W is hydrogen atom,
—$(C_1-C_6)$-alkyl, wherein alkyl is unsubstituted or mono-, di- or trisubstituted independently of one another by R2,
—$(C_3-C_8)$-cycloalkyl, wherein cycloalkyl is unsubstituted or mono-, di- or trisubstituted independently of one another by R2,
—$(C_6-C_{14})$-aryl, wherein aryl is unsubstituted or mono-, di-, tri- or four times substituted independently of one another by R2, or
—$(C_4-C_{14})$-heteroaryl ring system, which is as defined above, wherein heteroaryl is unsubstituted or mono-, di-, tri- or four times substituted independently of one another by R2, R1 and R2 are independent of one another identical or different and are
a) hydrogen atom,
b) —$(C_1-C_4)$-alkyl, wherein alkyl is unsubstituted or substituted one, two or three times by R13,
c) halogen,
d) phenyloxy-, wherein phenyloxy is unsubstituted or substituted one, two or three times by R13,
e) —$(C_1-C_3)$-fluoroalkyl,
f) —N(R10)-$(C_1-C_4)$-alkyl, wherein alkyl is unsubstituted or substituted one, two or three times by R13,
g) —$(C_6-C_{14})$-aryl, wherein aryl is unsubstituted or mono-, di-, tri- or four times substituted independently of one another by R13,
h) —$(C_4-C_{14})$-heteroaryl ring system, which is as defined above, wherein heteroaryl is unsubstituted or mono-, di-, tri- or four times substituted independently of one another by R13,
i) —$(C_3-C_8)$-cycloalkyl, wherein said cycloalkyl is unsubstituted or mono-, di-, tri- or four times substituted independently of one another by R13,
j) a 3- to 7-membered cyclic residue, containing 1, 2, 3 or 4 heteroatoms chosen from nitrogen, sulfur or oxygen, wherein said cyclic residue is unsubstituted or mono-, di-, tri- or four times substituted independently of one another by R13,
k) —O—CF$_3$,
l) —O—$(C_1-C_4)$-alkyl, wherein alkyl is unsubstituted or substituted one to three times by R13,
m) —NO$_2$,
n) —CN,
j) —OH,
p) —C(O)—R10,
q) —C(O)—O—R11,
r) —C(O)—N(R11)-R12,
s) —N(R11)-R12,
t) —N(R10)-SO$_2$—R10,
v) —S—R10,
w) —SO$_n$—R10, wherein n is 1 or 2,
x) —SO$_2$—N(R11)-R12 or
y) —Si(R11)(R11)-R12, or R1 and R2 form together with the atoms which they are attached to a 5- or 8-membered ring, containing up to 0, 1, 2, 3 or 4 heteroatoms chosen from nitrogen, sulfur or oxygen, wherein said ring is unsubstituted or substituted one, two, three or four times by R14, R10 is hydrogen atom, —$(C_1-C_3)$-fluoroalkyl or —$(C_1-C_6)$-alkyl, R11 and R12 are independently of one another identical or different and are
a) hydrogen atom,
b) —$(C_1-C_6)$-alkyl, wherein alkyl is unsubstituted or mono-, di- or trisubstituted independently of one another by R13,
c) —$(C_6-C_{14})$-aryl-, wherein aryl is unsubstituted or mono-, di- or trisubstituted independently of one another by R13, d) —(C$_4$-C$_{14}$)-heteroaryl ring system, which is as defined above, wherein heteroaryl is unsubstituted or mono-, di- or trisubstituted independently of one another by R13, R13 is halogen, —NO$_2$, —CN, =O, —OH, —(C$_1$-C$_8$)-alkyl, —(C$_1$-C$_8$)-alkoxy, —CF$_3$, phenyloxy-, —C(O)—R10, —C(O)—O—R17, —C(O)—N(R17)-R18, —S—R10, —N(R17)-R18, —N(R10)-SO$_2$—R10, —SO$_n$—R10, wherein n is 1 or 2, —SO$_2$—N(R17)-R18, —(C$_6$-C$_{14}$)-aryl, wherein aryl is unsubstituted or mono-, di- or trisubstituted independently of one another by R14, —(C$_4$-C$_{14}$)-heteroaryl ring system, which is as defined above, wherein heteroaryl is unsubstituted or mono-, di- or trisubstituted independently of one another by R14, —(C$_3$-C$_8$)-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, R14 is halogen, —OH, =O, —CN, —CF$_3$, —(C$_1$-C$_8$)-alkyl, —(C$_1$-C$_4$)-alkoxy, —NO$_2$, —C(O)—OH, —NH$_2$, —C(O)—O—(C$_1$-C$_4$)-alkyl, —(C$_1$-C$_8$)-alkylsulfonyl, —C(O)—NH—(C$_1$-C$_8$)-alkyl, —C(O)—N—[(C$_1$-C$_8$)-alkyl]$_2$, —C(O)—NH$_2$, —S—R10, —N(R10)-C(O)—NH—(C$_1$-C$_8$)-alkyl, or —N(R10)-C(O)—N—[(C$_1$-C$_8$)-alkyl]$_2$, R17 and R18 are independently of one another identical or different and are
a) hydrogen atom,
b) —(C$_1$-C$_6$)-alkyl,
c) —(C$_6$-C$_{14}$)-aryl- or
d) —(C$_4$-C$_{14}$)-heteroaryl ring system, which is as defined above, said process comprises reacting a compound of formula II

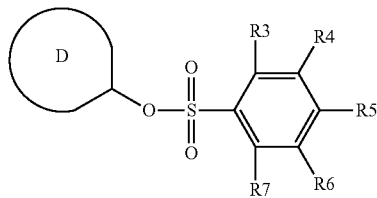

(II)

wherein D is as defined in formula I and
R3, R4, R5, R6 and R7 are independently of one another identical or different and are
a) hydrogen atom,
b) —(C$_1$-C$_4$)-alkyl,
c) halogen,
d) —(C$_1$-C$_3$)-fluoroalkyl,
e) —O—CF$_3$,
f) —NO$_2$,
g) —CN,
h) —OH,
i) —C(O)—R10,
j) —C(O)—O—R11,
k) —C(O)—N(R11)-R12,
l) —N(R11)-R12,
m) —SO$_n$—R10, wherein n is 1 or 2, or
n) —SO$_2$—N(R11)-R12, with a compound of formula III

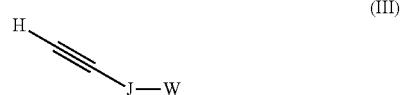

(III)

wherein J and W are as defined in formula I,
in the presence of a palladium catalyst, a base, a ligand and a protic solvent to give a compound of formula I and
optionally the compound of formula I is converted to its physiologically tolerated salt.

2) The present invention also relates to a process for the preparation of selected compounds of formula I, wherein
D is a (C$_4$-C$_{14}$)-heteroaryl ring system, wherein heteroaryl is selected from acridinyl, azaindole (1H-pyrrolo-pyridinyl), azabenzimidazolyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, chromanyl, chromenyl, furanyl, furazanyl, imidazolyl, indanyl, 1H-indazolyl, indolizinyl, indolyl, 3H-indolyl, isobenzofuranyl, isoindazolyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, 1,4-oxazepinyl, oxazolyl, phenanthridinyl, phenazinyl, phenothiazinyl, phenoxazinyl, phthalazinyl, pteridinyl, purinyl, pyrazinyl, pyrazolo[3,4-b]pyridine, pyrazolyl, pyridazinyl, pyridooxazolyl, pyridoimidazolyl, pyridothiazolyl, pyridinyl, pyridyl, pyrimidinyl, 2H-pyrrolyl, pyrrolyl, quinolinyl, 4H-quinolizinyl, quinoxalinyl, quinuclidinyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, 1,2-thiazinyl, 1,3-thiazinyl, 1,4-thiazinyl, 1,3-thiazolyl, thiazolyl, thienyl, thienothiazolyl, thienooxazolyl, thienoimidazolyl, thiophenolyl, thiophenyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl and wherein heteroaryl is unsubstituted or depending on the number of atoms is mono-, di-, tri- four- or five times substituted independently of one another by R1;

J is a covalent bond,
—(C$_1$-C$_6$)-alkylene, wherein alkylene is unsubstituted or mono-, di- or trisubstituted independently of one another by R2,
—(C$_3$-C$_6$)-cycloalkyl, wherein cycloalkyl is unsubstituted or mono-, di- or trisubstituted independently of one another by R14,
phenyl, wherein phenyl is unsubstituted or mono-, di-, tri- or four times substituted independently of one another by R13, or
—(C$_4$-C$_{14}$)-heteroaryl, wherein heteroaryl is as defined above and is unsubstituted or mono-, di-, tri- or four times substituted independently of one another by R13, W is hydrogen atom,
—(C$_1$-C$_6$)-alkyl, wherein alkyl is unsubstituted or mono-, di- or trisubstituted independently of one another by R2,
—(C$_3$-C$_6$)-cycloalkyl, wherein cycloalkyl is unsubstituted or mono-, di- or trisubstituted independently of one another by R2,
phenyl, wherein phenyl is unsubstituted or mono-, di-, tri- or four times substituted independently of one another by R2, or —($C_4$-$C_{14}$)-heteroaryl, wherein heteroaryl is as defined above and is unsubstituted or mono-, di-, tri- or four times substituted independently of one another by R2;

R1 and R2, are independent of one another identical or different and are
  a) hydrogen atom,
  b) F,
  c) Cl,
  d) —($C_1$-$C_4$)-alkyl, wherein alkyl is unsubstituted or substituted one to three times by R13,
  e) —($C_1$-$C_3$)-fluoroalkyl,
  f) phenyl, wherein phenyl is unsubstituted or substituted one to three times by R13,
  g) —($C_4$-$C_{14}$)-heteroaryl, wherein heteroaryl is as defined above and is unsubstituted or mono-, di-, tri- or four times substituted independently of one another by R13,
  h) —($C_3$-$C_8$)-cycloalkyl, wherein said cycloalkyl is unsubstituted or mono-, di-, tri- or four times substituted independently of one another by R13,
  i) a 3- to 7-membered cyclic residue, wherein the cyclic residue is selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole and 1,2,4-triazole, and wherein said cyclic residue is unsubstituted or mono-, di-, tri- or four times substituted independently of one another by R13,
  j) —O—$CF_3$,
  k) —O—($C_1$-$C_4$)-alkyl, wherein alkyl is unsubstituted or substituted one to three times by R13,
  l) —N(R10)-($C_1$-$C_4$)-alkyl, wherein alkyl is unsubstituted or substituted one to three times by R13,
  m) —CN,
  n) —OH,
  o) phenyloxy-, wherein phenyloxy is unsubstituted or substituted one to three times by R13,
  p) —C(O)—O—R11,
  q) —C(O)—N—(R11)-R12,
  r) —N(R11)-R12,
  s) —N(R10)-$SO_2$—R10,
  t) —S—R10,
  v) —$SO_n$—R10, wherein n is 1 or 2,
  w) —$SO_2$—N(R11)-R12,
  x) —C(O)—R10,
  y) —Si(R11)(R11)-R12, R10 is hydrogen atom, —($C_1$-$C_3$)-fluoroalkyl or —($C_1$-$C_6$)-alkyl, R11 and R12 are independently of one another identical or different and are
  a) hydrogen atom,
  b) —($C_1$-$C_4$)-alkyl, wherein alkyl is unsubstituted or mono-, di- or trisubstituted independently of one another by R13,
  c) phenyl, wherein phenyl is unsubstituted or mono-, di- or trisubstituted independently of one another by R13, or
  d) —($C_4$-$C_{14}$)-heteroaryl, wherein heteroaryl is as defined above and is unsubstituted or mono-, di- or trisubstituted independently of one another by R13, R13 is F, Cl, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N(R17)-R18, —N(R17)-R18, —S—R10, —N(R10)-$SO_2$—R10, —$SO_n$—R10, wherein n is 1 or 2, —$SO_2$—N(R17)-R18, phenyl, wherein phenyl is unsubstituted or mono-, di- or trisubstituted independently of one another by R14, —($C_4$-$C_{14}$)-heteroaryl, wherein heteroaryl is as defined above and is unsubstituted or mono-, di- or trisubstituted independently of one another by R14, —($C_3$-$C_6$)-cycloalkyl, wherein said cycloalkyl is unsubstituted or mono-, di- or trisubstituted independently of one another by R14, or a 3- to 7-membered cyclic residue, wherein said cyclic residue is as defined above and is unsubstituted or mono-, di- or trisubstituted independently of one another by R14, R14 is F, Cl, —OH, =O, —CN, —$CF_3$, —($C_1$-$C_8$)-alkyl, —($C_1$-$C_4$)-alkoxy, —C(O)—OH, —$NH_2$, —C(O)—O—($C_1$-$C_4$)-alkyl, —($C_1$-$C_8$)-alkylsulfonyl, —C(O)—$NH_2$, —C(O)—NH—($C_1$-$C_8$)-alkyl, —C(O)—N—[($C_1$-$C_8$)-alkyl]$_2$, —S—R10, —N(R10)-C(O)—NH—($C_1$-$C_8$)-alkyl or —N(R10)-C(O)—N—[($C_1$-$C_8$)-alkyl]$_2$, R17 and R18 are independently of one another identical or different and are
  a) hydrogen atom,
  b) —($C_1$-$C_4$)-alkyl,
  c) phenyl or
  d) —($C_4$-$C_{14}$)-heteroaryl, wherein heteroaryl is as defined above, and R3, R4, R5, R6 and R7 are independently of one another identical or different and are
  a) hydrogen atom,
  b) —($C_1$-$C_4$)-alkyl,
  c) halogen,
  d) —($C_1$-$C_3$)-fluoroalkyl,
  e) —O—$CF_3$,
  f) —$NO_2$,
  g) —CN,
  h) —OH,
  i) —C(O)—R10,
  j) —C(O)—O—R11,
  k) —C(O)—N(R11)-R12,
  l) —N(R11)-R12,
  m) —$SO_n$—R10, wherein n is 1 or 2, or
  n) —$SO_2$—N(R11)-R12.

3) The present invention also relates to a process for the preparation of selected compounds of formula I, wherein D is a ($C_4$-$C_{14}$)-heteroaryl ring system, wherein heteroaryl is selected from 1H-indazolyl, pyrazolyl, pyridyl, pyrimidinyl, quinolinyl and thienyl, and wherein heteroaryl is unsubstituted or is mono- or disubstituted independently of one another by R1;

J is a covalent bond, —($C_1$-$C_4$)-alkylene, cyclohexenyl, cyclohexyl, phenyl, wherein phenyl is unsubstituted or mono- or disubstituted independently of one another by R13, or thienyl, W is hydrogen atom, —($C_1$-$C_4$)-alkyl, cyclohexenyl, cyclohexyl, phenyl, wherein phenyl is unsubstituted or mono- or disubstituted independently of one another by R2, or thienyl, R1 and R2, are independent of one another identical or different and are
  a) hydrogen atom,
  b) F,
  c) Cl,
  d) —($C_1$-$C_4$)-alkyl, wherein alkyl is unsubstituted or substituted one time by R13,
  e) —($C_1$-$C_3$)-fluoroalkyl,
  f) phenyl, wherein phenyl is unsubstituted or substituted one or two times by R13,
  g) —O—($C_1$-$C_4$)-alkyl, wherein alkyl is unsubstituted or substituted one or two times by R13,
  h) —N(R10)-($C_1$-$C_4$)-alkyl, wherein alkyl is unsubstituted or substituted one or two times by R13,
  i) —CN,
  j) —OH,
  k) —C(O)—O—R11 or
  l) —N(R11)-R12,
R10 is hydrogen atom or —($C_1$-$C_4$)-alkyl,
R11 and R12 are independently of one another identical or different and are hydrogen atom or —($C_1$-$C_4$)-alkyl,
R13 is F, Cl, —CN, —OH, —($C_1$-$C_4$)-alkyl, —$CF_3$, phenyl or —N(R17)-R18,
R17 and R18 are independently of one another identical or different and are hydrogen atom or —($C_1$-$C_4$)-alkyl, and
R3, R4, R5, R6 and R7 are independently of one another identical or different and are hydrogen atom or —($C_1$-$C_4$)-alkyl.

The protic solvent useful in the process of the present invention must be solvent, wherein the compounds of formulae II and III, palladium catalyst, base and ligand are soluble or at least partially soluble and compatible and is chemically inert under the reaction conditions and does not contain oxygen as impurity.

Examples of said protic solvents are: water, methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol. Preferred is i-butanol, t-butanol, 2-methylbutan-2-ol, 3-methyl-3-pentanol, 3-ethyl-3-pentanol. Most preferred is t-butanol.

The base useful in this process of the present invention is a basic organic or inorganic compound and acts as proton acceptor without inhibiting the catalytic activity of the employed palladium. Suitable classes of such bases are for example carbonates, phosphates, fluorides, alkoxides and hydroxides with a suitable metal as counter ion. Carbonates and phosphates are the preferred bases in the process of the present invention. Potassium carbonate or cesium carbonate and in particular potassium phosphate are the preferred bases.

The bases are generally employed in moderate excess based on the heteroaryl-1-tosylate of the compound of formula II. A useful range is a 1.5 to 4 fold excess based on the heteroaryl-1-tosylate of the compound of formula II. The base may be favorably employed in a 3 fold excess based on the heteroaryl-1-tosylate of the compound of formula II.

The palladium catalysts useful in this process are not bound to solid carriers such as zeolite or silica and can be selected from the following classes: Pd-alkanoates, Pd-alkanoate complexes, Pd-acetonates, Pd-halides, Pd-halide complexes, Pd-phosphine complexes. Representative examples include, but are not limited to, provided that the catalyst contains no monophosphino-biphenyl derivative as a ligand: palladium (II) acetate, palladium (II) trifluoroacetate, palladium (II) hexafluoro-acetylacetonate, palladium (II) bromide, palladium (II) chloride, palladium (II) iodide, palladium (II) nitrate, palladium (II) acetylacetonate, dichlorobis-acetonitrile palladium (II), tetrakis(triphenylphosphine) palladium (0), trans-di(μ-acetato)bis[o-(di-o-tolylphosphino)benzyl]dipalladium (II), tris (dibenzylideneacetone)dipalladium(0), tris (dibenzylideneacetone)dipalladium(0) chloroform adduct, palladium (II) chloride, 2,2'-bis(diphenylphosphino)-1,1'-binaphthylpalladium(II) chloride, acetato(2'-di-tert-butylphosphino-1,1'-biphenyl-2-yl)palladium(II), (1,2-Bis(diphenylphosphino)ethane)di-chloropalladium(II), Bis[1,2-bis (diphenylphosphino)ethane]palladium (0), [(2S,3S)-Bis (diphenylphosphino)butane][eta3-allyl]palladium(II) perchlorate, 1,3-bis(2,4,6-trimethylphenyl)imidazol-2-ylidene(1,4-naphthoquinone)palladium (0) dimer, [P,P'-1,3-bis(di-1-propylphosphino)propane][P-1,3-bis(di-1-propylphosphino)propane]palladium (0), 2-(dimethylamino) ferrocen-1-yl-palladium(II) chloride dinorbornylphosphine complex, chloro(di-2-norbornylphosphino)(2-dimethylaminomethylferrocen-1-yl)palladium (II), 1,1'-bis(diphenylphosphino)ferrocene palladium (II) chloride, dichloro[1, 1'-bis(diphenylphosphino)ferrocene]palladium (II) dichloromethane adduct, dichloro((S)—N,N-dimethyl-1-((R)-2-(diphenylphosphino)ferrocenyl)ethylamine)-palladium, (1,1'-bis(diphenylphosphino)ferrocene)palladium(II) chloride, [(2S)-1-[(1S)-1-[bis(1,1-dimethylethyl)phosphino-kappaP]ethyl]-2-(diphenylphosphino-kappaP)ferrocene] palladium dichloride, [(2S)-1-[(1S)-1-[bis(1,1-dimethylethyl)-phosphino-kappaP]ethyl]-2-(diphenylphosphino-kappaP)ferrocene][tris(2-methylphenyl)phosphine] palladium, [(2R)-1-[(1R)-1-[bis(1,1-dimethylethyl)-phosphino-kappaP]ethyl]-2-(dicyclohexylphosphino-kappaP)ferrocene][tris(2-methylphenyl)phosphine] palladium. The preferred catalysts are palladium (II) acetate and in particular palladium (II) trifluoroacetate.

The palladium catalyst is generally employed in an amount in the range of 1 to 10 mole percent based on the heteroaryl-1-tosylate of the compound of formula II. A useful range is 1 to 9 mole percent of palladium catalyst based on the heteroaryl-1-tosylate of the compound of formula II.

The ligand useful in this process is a mono- or bidentate phosphine ligand and can be selected from the following compounds, but are not limited to, provided that the phosphine ligand is not a monophosphino-biphenyl derivative: (+/−)-2,2'-bis(diphenylphosphino)-1,1'-binaphthalene, (9,9-dimethyl-9h-xanthene-4,5-diyl)bis[diphenyl phosphine], (R)-(−)-1-[(S)-2-(diphenylphosphino)ferrocenyl]ethyldicyclohexylphosphine, 1,2-Bis(diphenylphosphino)ethane, (2S, 3S)-(−)-bis(diphenylphosphino)butane, 1,3-Bis(diphenylphosphino)propane, (R)-(−)-1-[(S)-2-(Dicyclohexylphosphino)ferrocenyl]-ethyldi-tert-butylphosphine, (R)-(+)-1,1'-Bis(diphenylphosphino)-2,2'-bis(N,N-diisopropylamido)ferrocene, (S,S)-1-[1-(Di-tert-butylphosphino)ethyl]-2-(diphenylphosphino)ferrocene, (1R,2R)-(+)-1,2-Diaminocyclohexane-N,N'-bis(2-diphenylphosphino-1-naphtoyl, (−)-1,2-Bis((2S,5S)-2,5-diisopropylpholano)-benzene, Bis[(2-diphenylphosphino) phenyl]ether, (S)-(−)-2,2'-Bis(di-para-tolylphosphino)-1,1'-binaphyl, 4,5-Bis(bis(3,5-bis(trifluoromethyl)phenyl)-phosphino)-9,9-dimethylxanthen, (R)-(−)-1-[(S)-2-(di(3,5-bis-trifluoromethylphenyl)phosphino)ferrocenyl] ethyldicyclohexylphosphine, (R)-(−)-1-[(S)-2-(di(3,5-bis-trifluoromethylphenyl)phosphino)ferrocenyl]ethyldi(3,5-dimethylphenyl)phosphine, 2,2'-bis[(2',4',6'-triisopropyl) dicyclohexylphosphino]-biphenyl, 2,2'-bis(di-tertbutylphosphino)biphenyl, (R)-(+)-1-[(R)-2-(2'-di(3,5-xylyl)phosphinophenyl)ferrocenyl]ethyldi(3,5-xylyl9phosphine, (R)-(−)-1-[(S)-2-(bis(3,5-dimethyl-4-methoxyphenyl)phosphino)ferrocenyl]ethyldicyclohexyl-phosphine, (R)-(+)-1-[(R)-2-(2'-di(3,5-dimethyl-4-methoxyphenyl)phosphinophenyl)-ferrocenyl]ethyldi(bis-3,5-trifluoromethylphenyl)phosphine, (R)-(−)-1-[(S)-2-(dicyclohexylphosphino)ferrocenyl]ethyldi-t-butylphosphine, (R)-(−)-1-[(S)-2-bis(4-trifluoromethylphenyl)phosphino)ferrocenyl]ethyl-di-t-butylphosphine, (1,1'-ferrocenediyl)phenylphosphine, (R)-(+)-1,1'-bis(diphenylphosphino)-2,2'-bis(N,N-diisopropylamido)ferrocene, 1,2,3,4,5-pentaphenyl-1'-(di-t-butylphosphino)-ferrocene, (S)-(+)-1-[(R)-2-(diphenylphosphino)ferrocenyl]ethyldi-t-butylphosphine, (R)-(−)-1-[(S)-2-(diphenylphosphino)ferrocenyl]ethyldi-t-butylphosphine, (S)-(+)-1-[(R)-2-(dicyclohexylphosphino)ferrocenyl]ethyldiphenylphosphine, 1,1'-bis(di-1-propylphosphino)ferrocene, (R)-(−)-1-[(S)-2-(dicyclohexylphosphino)ferrocenyl]ethyl-diphenylphosphine, (S)-(+)-1-[(R)-2-(dicyclohexylphosphino)ferrocenyl]ethyldicyclohexylphosphine, (R)-(−)-1-[(S)-2-(dicyclohexylphosphino)ferrocenyl]ethyldicyclohexylphosphine, (R)-(−)-1-[(S)-2-(diphenylphosphino)ferrocenyl]ethyldicyclohexylphosphine, 1,1'-bis(di-tert-butylphosphino)ferrocene, (−)-(R)-1-((S)-2-(diphenylphosphino)ferrocenyl)ethyl methyl ether, (+)-(S)-1-((R)-2-(diphenyl-phosphino)ferrocenyl)ethyl methyl ether, (+)-(S)—N,N-dimethyl-1-((R)-1',2-bis(diphenylphosphino)ferrocenyl)ethylamine, (+)-(S)—N,N-dimethyl-1-((R)-2-(diphenylphosphino)ferrocenyl)ethylamine, 1,1'-bis(diphenylphosphino)ferrocene, tri-tert-butylphosphine, di-tert-butylmethylphosphonium tetrafluoroborate, tri-2-furylphosphine Most favorably are 1-[2-(dicyclohexylphosphino)ferrocenyl]ethyldi-t-butylphosphine, 1-[2-(diphenylphosphino)ferrocenyl]ethyldi-t-butylphosphine are employed in particular in combination with a palladium source bearing no phosphine itself, like e.g. dichloro-bis-acetonitrile palladium (II), palladium (II) bromide, palladium (II) iodide, palladium (II) acetate, palladium (II) trifluoroacetate, tris(dibenzylideneacetone)dipalladium(0), palladium (II) chloride. The most preferred ligand is 1-[2-(dicyclohexylphosphino)-ferrocenyl]ethyldi-t-butylphosphine.

The phosphine ligand is generally employed in an amount in the range of 1 to 15 mole percent based on the heteroaryl-1-tosylate of the compound of formula II. A useful range is 1 to 10 mole percent of phosphine ligand based on the heteroaryl-1-tosylate of the compound of formula II. Most favourably the phosphine ligand is employed in a range of 1.5-3 ratio in particular a 2.3 ratio with respect to the palladium source.

The reaction is carried out in the temperature range 60° C. to 150° C. A useful temperature is about 70° C. to 100° C. Generally the reaction is carried out under the exclusion of air like e.g. in an argon or nitrogen atmosphere at atmospheric pressure. The reaction time is in the range of 3 to 48 hours (h).

The progress of each reaction may be monitored by methods known to those skilled in the art, like for example thin layer silica gel chromatography, gas chromatography, nuclear magnetic resonance, infrared spectroscopy, and high pressure liquid chromatography combined with ultraviolet detection or mass spectroscopy. Preferably thin layer silica gel chromatography and high pressure liquid chromatography (HPLC) combined with mass spectroscopy are used.

The isolation and purification procedures useful for the compounds obtained by the process of the present invention are well-known to those skilled in the art, like for example filtration through a celite containing cartridge, aqueous work-up, extraction with organic solvents, distillation, crystallization, chromatography on silica, and high pressure liquid chromatography on normal phase or reversed phase. Preferred methods include, but are not limited to those exemplified.

The term alkyl as used herein expressly includes saturated groups as well as unsaturated groups which latter groups contain one or more, for example one, two or three, double bonds and/or triple bonds. All these statements also apply if an alkyl group occurs as a substituent on another residue, for example in an alkyloxy residue, an alkyloxycarbonyl residue or an arylalkyl residue. Examples of "—($C_1$-$C_8$)-alkyl" or "—($C_1$-$C_8$)-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. Unsaturated alkyl residues are e.g. alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted.

The term "—($C_3$-$C_8$)-cycloalkyl" is understood as cyclic alkyl residues are cycloalkyl residues containing 3, 4, 5, 6, 7 or 8 ring carbon atoms like cyclopropyl, cyclobutyl, cyclopentyl, cyclohexyl, cyloheptyl or cyclooctyl, which can also be unsaturated. Unsaturated cycloalkyl groups are e.g. cyclopentenyl or cyclohexenyl. The term "—($C_6$-$C_{14}$)-aryl" is understood as meaning aromatic hydrocarbon radicals containing from 6 to 14 carbon atoms in the ring. Examples of —($C_6$-$C_{14}$)-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The term "—($C_4$-$C_{14}$)-heteroaryl" refers to a 4- to 14-membered aromatic cyclic residue, which consists depending on the number of ring atoms out of one, two or three ring systems, wherein one or more of the 4 to 14 ring carbon atoms are replaced by heteroatoms such as nitrogen, oxygen or sulfur. —($C_4$-$C_{14}$)-Heteroaryl compounds are formally derived from aryls by replacement of one or more methine (—C≡) and/or vinylene (—CH=CH—) groups by trivalent or divalent heteroatoms, respectively, in such a way as to maintain the continuous p-electron system characteristic of aromatic systems and a number of out-of-plane p-electrons corresponding to the Hückel rule (4n+2); an alternative term is hetarenes. Examples are acridinyl, azaindole (1H-pyrrolopyridinyl), azabenzimidazolyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, chromanyl, chromenyl, furanyl, furazanyl, imidazolyl, indanyl, 1H-indazolyl, indolizinyl, indolyl, 3H-indolyl, isobenzofuranyl, isoindazolyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, 1,4-oxazepinyl, oxazolyl, phenanthridinyl, phenazinyl, phenothiazinyl, phenoxazinyl, phthalazinyl, pteridinyl, purinyl, pyrazinyl, pyrazolo[3,4-b]pyridine, pyrazolyl, pyridazinyl, pyridooxazolyl, pyridoimidazolyl, pyridothiazolyl, pyridinyl, pyridyl, pyrimidinyl, 2H-pyrrolyl, pyrrolyl, quinolinyl, 4H-quinolizinyl, quinoxalinyl, quinuclidinyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, 1,2-thiazinyl, 1,3-thiazinyl, 1,4-thiazinyl, 1,3-thiazolyl, thiazolyl, thienyl, thienothiazolyl, thienooxazolyl, thienoimidazolyl, thiophenolyl, thiophenyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "a 3- to 7-membered cyclic residue, containing 1, 2, 3 or 4 heteroatoms" refer to structures of heterocycles, which are residues such as azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The 3- to 7-membered cyclic residue may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl.

The term "R1 and R2, R2 and R3, R3 and R4 or R4 and R5 form together with the atoms which they are attached to a 5- or 8-membered ring, containing up to 0, 1, 2, 3 or 4 heteroatoms chosen from nitrogen, sulfur or oxygen" refers to residues which are e.g. azepine, azirine, azocane, azocane-2-one, cyloheptyl, cyclohexyl, cyclooctane, cyclooctene, 1,4-diazepane, 1,2-diazepine, 1,3-diazepine, 1,4-diazepine, [1,2]diazocan-3-one, [1,3]diazocan-2-one, [1,4]diazocane, dioxazine, dioxazole, [1,4]dioxocane, 1,3-dioxolane, dioxole, 1,3-dioxolene, furan, imidazole, imidazolidine, imidazoline, isothiazole, isothiazolidine, isothiazoline, isothiazole, isoxazole, isoxazolidine, isoxazoline, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxaziridine, [1,4]oxazocane, [1,3]oxazocan-2-one, oxocane, oxocan-2-one, oxazole, piperidine, piperazine, phenyl, pyridazine, pyridine, pyrimidine, pyran, pyrazine, pyrazole, pyrazolepyrrole, pyrazolidine, pyrazoline, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, tetrazole, thiadiazine, thiadiazole, 1,2-thiazine, 1,3-thiazine, 1,4-thiazine, thiazole, 1,3-thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "—($C_1$-$C_3$)-fluoroalkyl" is a partial or totally fluorinated alkyl-residue, which can be derived from residues such as —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

Halogen is fluorine, chlorine, bromine or iodine, preferably fluorine, chlorine or bromine, particularly preferably chlorine or bromine.

The term "tosylate" or "Tos" refers to p-toluenesulfonic acid ester or p-toluenesulfonate.

The term "triflate" or "Tf" refers to trifluoro-methanesulfonic acid ester or trifluoromethanesulfonate.

The term "nonaflate" refers to 1,1,2,2,3,3,4,4,4-nonafluoro-1-butanesulfonic acid ester or 1,1,2,2,3,3,4,4,4-nonafluoro-1-butanesulfonate.

The term "homogenous palladium catalyzed Sonogashira reaction" refers to a reaction system wherein the palladium catalyst is not bond to a solid carrier such as zeolite or silica.

Optically active carbon atoms present in the compounds of the formula (I) can independently of each other have R configuration or S configuration. The compounds of the formula (I) can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula (I), and it comprises all ratios of the stereoisomers in the mixtures. In case the compounds of the formula (I) can be present as E isomers or Z isomers (or cis isomers or trans isomers) the invention relates both to pure E isomers and pure Z isomers and to E/Z mixtures in all ratios. The invention also comprises all tautomeric forms of the compounds of the formula (I).

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula (I) can also be obtained by employing stereochemically uniform starting materials or by using stereoselective reactions.

The starting materials or building blocks for use in the general synthetic procedures that can be applied in the preparation of the compounds of formula (I) are readily available to one of ordinary skill in the art. In many cases they are commercially available or have been described in the literature. Otherwise they can be prepared from readily available precursor compounds analogously to procedures described in the literature, or by procedures or analogously to procedures described in this application.

Further, in order to obtain the desired substituents in the heteroaryl nucleus of the ring system in the formula I, the functional groups introduced into the ring system during the cross-coupling reaction can be chemically modified. For example, a heteroaryl ring carrying a hydrogen atom at the 2-position can be obtained by oxidation of 2-methyl heteroaryl-1-alkyne to the heteroaryl-1-alkyne-2-carboxylic acid and subsequent decarboxylation or from heteroaryl-1-alkynes carrying an ester group in the respective position. Carboxylic acid groups and acetic acid groups at the 2-position for example can be converted into their homologues by usual reactions for chain elongation of carboxylic acids.

Especially the groups present in heteroaryl ring system can be modified by a variety of reactions and thus the desired residues denoted by R1 be obtained. For example, nitro groups can be reduced to amino group with under the described reaction conditions or by various reducing agents, such as sulfides, dithionites complex hydrides or by catalytic hydrogenation. A reduction of a nitro group may also be carried out at a later stage of the synthesis of a compound of the formula (I), and a reduction of a nitro group to an amino group may also occur simultaneously with the reaction performed on another functional group, for example when reacting a group like a cyano group with hydrogen sulfide or when hydrogenating a group. Ester groups present in the heteroaryl nucleus can be hydrolyzed to the corresponding carboxylic acids, which after activation can then be reacted with amines or alcohols under standard conditions. Ether groups present at the benzene nucleus, e.g. benzyloxy groups or other easily cleavable ether groups, can be cleaved to give hydroxyl groups which then can be reacted with a variety of agents, for example etherification agents or activating agents allowing replacement of the hydroxyl group by other groups. Sulfur-containing groups can be reacted analogously.

Due to the fact that in the present case the functional groups are attached to an heteroaryl ring it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques. However, finding out suitable reaction variants and reaction conditions in such cases does not cause any problems for one skilled in the art.

In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art. As example of a precursor group cyano groups may be mentioned, which can in a later reaction step be transformed into carboxylic acid derivatives or reduced to an aminomethyl group. Protective groups can also have the meaning of a solid phase, and cleavage from the solid phase stands for the removal of the protective group. The use of such techniques is known to those skilled in the art. For example, a phenolic hydroxy group can be attached to a trityl-polystyrene resin, which serves as a protecting group, and the molecule is cleaved from this resin by treatment with trifluoroacetate at a later stage of the synthesis.

In the course of the synthesis the employment of microwave assistance for speeding-up, facilitating or enabling reactions may be beneficial or even required in many cases. Some reactions are for example described by P. Lidstrom, J. Tierney, B. Wathey, J. Westman, Tetrahedron, 57 (2001), 9225;

Physiologically tolerable salts of the compounds of formula I are nontoxic salts that are physiologically acceptable, in particular, pharmaceutically utilizable salts. Such salts of compounds of formula I containing acidic groups, for example, a carboxyl group (COOH), include, for example, alkali metal salts or alkaline earth metal salts, such as sodium salts, potassium salts, magnesium salts and calcium salts, as well as salts with physiologically tolerable quaternary ammonium ions, such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of formula I, for example, amino groups or guanidino groups, form acid addition salts, for example, with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, for example, a guanidino group and a carboxyl group, can also be present as zwitterions (betaines) which are likewise included in the scope of the present invention.

Salts of compounds of formula I can be obtained by customary methods known to those skilled in the art, for example, by combining a compound of the formula I with an inorganic or organic acid or base in a solvent or dispersant, or from other salts by cation exchange or anion exchange. The present invention also includes all salts of the compounds of formula I which, because of low physiologically tolerability, are not directly suitable for use in pharmaceuticals but are suitable, for example, as intermediates for carrying out further chemical modifications of the compounds of formula I or as starting materials for the preparation of physiologically tolerable salts.

A further aspect of the invention is the use of a compound of the formula I as prepared by the process according to the invention for the production of pharmaceuticals, diagnostic agents, liquid crystals, polymers, herbicides, fungicidals, nematicidals, parasiticides, insecticides, acaricides and arthropodicides. Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

EXAMPLES

| Abbreviations: | |
|---|---|
| Argon | Ar |
| tert-Butyl | tBu |
| dibenzylidenacetone | dba |
| dichloromethane | DCM |
| N,N-dimethyl4-aminopyridine | DMAP |
| 1,1'-Bis(diphenylphosphino)ferrocene | DPPF |
| Triethylamine | Et$_3$N |
| Ethylacetate | EtOAc |
| Fast atom bombardment | FAB |
| High pressure liquid chromatography | HPLC |
| Liquid chromatography with mass spectrometry | LC-MS |
| Room temperature 21° C. to 24° C. | RT |
| Thin layer chromatography | TLC |
| Trifuoroacetate | TFA |
| 1-[2-(dicyclohexylphosphino)ferrocenyl]ethyldi-t-butylphosphine | Cy-PF-t-Bu. |

General Procedure for the Preparation of Heteroaryl-Tosylates and Heteroaryl Benzene-Sulfonic Acid Esters:

To a solution of the desired heteroaryl alcohol (13.23 mmol) in DCM (150 mL) were added, under stirring, Et$_3$N (17.20 mmol), DMAP (0.4 mmol) and p-toluenesulfonyl chloride (14.55 mmol) (or benzenesulfonyl chloride) successively. The resulting solution was stirred at RT until the starting material had been consumed (TLC and LCMS). The reaction mixture was then poured into a 1N HCl solution (100 mL) and extracted with DCM. The combined organic layers were washed with a saturated solution of NaHCO$_3$, brine and then dried over Na$_2$SO$_4$. The filtrate was concentrated under reduced pressure. When necessary, the residue obtained was purified by flash chromatography yielding the sulfonic ester compound of formula II.

General Procedure for the Sonogashira Cross-Coupling Reaction:

Under an Ar atmosphere, a dry reaction tube was charged with the heteroaryl sulfonic ester of the formula II (0.5 mmol), palladium trifluoroacetate (5 mg, 0.015 mmol), Cy-PF-t-Bu (19.4 mg, 0.035 mmol) and K$_3$PO$_4$ (318 mg, 1.50 mmol). 2 mL of t-BuOH were then added followed by the addition of 1-alkyne of the formula III (1 mmol). The tube was again purged with Ar, sealed and the reaction mixture was heated at 85° C. until the starting material had been consumed (TLC and LCMS). The reaction mixture was cooled to RT, diluted with EtOAc and filtered through a pad of Celite®. The filtrate was concentrated under reduced pressure and the residue was purified by flash chromatography on silica gel. The fractions containing the product were combined and the solvents were evaporated under reduced pressure to yield the desired heteroaryl-alkyne product of formula I.

Example 1

1-Methyl-3-(5-phenyl-pent-1-ynyl)-5-trifluoromethyl-1H-pyrazole

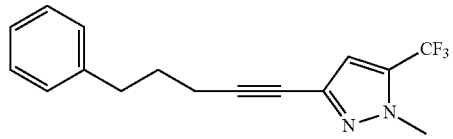 [SMILES: Cn1nc(C#CCCCc2ccccc2)cc1C(F)(F)F]

This product was prepared from toluene-4-sulfonic acid 1-methyl-5-trifluoromethyl-1H-pyrazol-3-yl ester and pent-4-ynyl-benzene following the general procedure for the Sonogashira cross-coupling reaction described above. Chromatography eluent: heptane/DCM 7:3; yield (86 mg, 60%); $^1$H NMR δ (CDCl$_3$): 7.31-7.25 (m, 2H), 7.22-7.16 (m, 3H), 6.64 (s, 1H), 3.98 (s, 3H), 2.78 (t, J=7.44 Hz, 2H), 2.42 (t, J=7.04 Hz, 2H), 1.95 (p, J=7.33 Hz, 2H); LCMS m/z: 292.

Example 2

3-Hept-1-ynyl-1-methyl-5-trifluoromethyl-1H-pyrazole

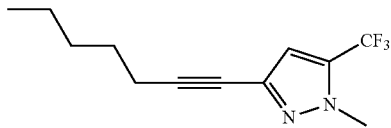 [SMILES: CCCCCC#Cc1cc(C(F)(F)F)n(C)n1]

This product was prepared from toluene-4-sulfonic acid 1-methyl-5-trifluoromethyl-1H-pyrazol-3-yl ester and 1-heptyne following the general procedure for the Sonogashira cross-coupling reaction described above. Chromatography eluent: heptane/DCM 7:3; yield (100 mg, 82%); $^1$H NMR δ (CDCl$_3$): 6.63 (s, 1H), 3.95 (s, 3H), 2.38 (t, J=7.34 Hz, 2H), 1.64-1.56 (m, 2H), 1.46-1.28 (m, 4H), 0.90 (t, J=7.36 Hz, 3H); LCMS m/z: 244.

Example 3

3-cyclohex-1-enylethynyl-1-methyl-5-trifluoromethyl-1H-pyrazole

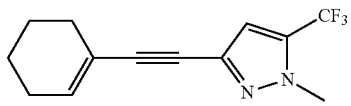 [SMILES: Cn1nc(C#CC2=CCCCC2)cc1C(F)(F)F]

This product was prepared from toluene-4-sulfonic acid 1-methyl-5-trifluoromethyl-1H-pyrazol-3-yl ester and 1-ethynyl-cyclohexene following the general procedure for the Sonogashira cross-coupling reaction described above. Chromatography eluent: heptane/DCM 7:3; yield (80 mg, 63%); ¹H NMR δ (CDCl₃): 6.63 (s, 1H), 6.27-6.29 (m, 1H), 3.96 (s, 3H), 2.14-2.22 (m, 4H), 1.73-1.58 (m, 4H); LCMS m/z: 254.

Example 4

1-Methyl-3-phenylethynyl-5-trifluoromethyl-1H-pyrazole

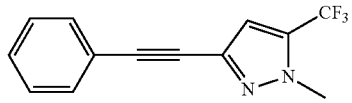 [SMILES: Cn1nc(C#Cc2ccccc2)cc1C(F)(F)F]

This product was prepared from toluene-4-sulfonic acid 1-methyl-5-trifluoromethyl-1H-pyrazol-3-yl ester and phenylacetylene following the general procedure for the Sonogashira cross-coupling reaction described above. Chromatography eluent: heptane/DCM 7:3; yield (19 mg, 15%); ¹H NMR δ (CDCl₃): 7.66-7.55 (m, 5H), 6.64 (s, 1H), 3.98 (s, 3H), LCMS m/z: 250.

Example 5

1-Methyl-3-phenyl-5-(5-phenyl-pent-1-ynyl)-1H-pyrazol-3-ylethynyl)-phenylamine

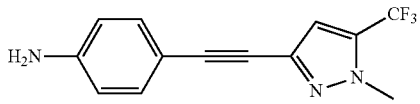 [SMILES: Cn1nc(C#Cc2ccc(N)cc2)cc1C(F)(F)F]

This product was prepared from toluene-4-sulfonic acid 1-methyl-5-trifluoromethyl-1H-pyrazol-3-yl ester and 4-ethynyl-phenylamine following the general procedure for the Sonogashira cross-coupling reaction described above. Chromatography eluent: heptane/DCM 7:3; yield (85 mg, 63%); ¹H NMR δ (CDCl₃): 7.62 (d, J=8.60 Hz, 2H), 7.55 (d, J=8.61 Hz, 2H), 6.64 (s, 1H), 4.01 (s, 3H), 3.82 (s, 2H); LCMS m/z: 265.

Example 6

1-Methyl-3phenyl-5-(5-phenyl-pent-1-ynyl)-1H-pyrazole

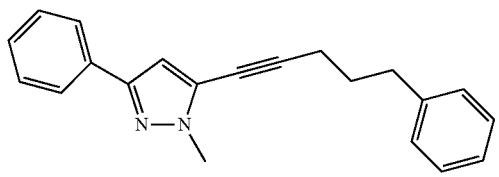 [SMILES: Cn1nc(-c2ccccc2)cc1C#CCCCc1ccccc1]

This product was prepared from toluene-4-sulfonic acid 2-methyl-5-phenyl-2H-pyrazol-3-yl ester and pent-4-ynyl-benzene following the general procedure for the Sonogashira cross-coupling reaction described above. Chromatography eluent: heptane/DCM 1:1; yield (80 mg, 53%); ¹H NMR δ (CDCl₃): 7.78 (d, J=8.21 Hz, 2H), 7.43-7.22 (m, 8H), 6.62 (s, 1H), 3.98 (s, 3H), 2.78 (t, J=7.30 Hz, 2H), 2.43 (t, J=7.19 Hz, 2H), 1.96 (p, J=7.33 Hz, 2H); LCMS m/z: 300.

Example 7

5-hept-1-ynyl-1-methyl-3-phenyl-1H-pyrazole

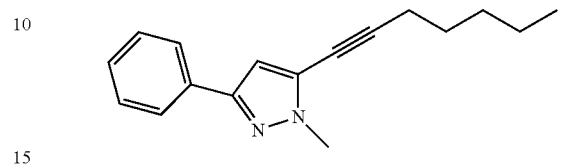

This product was prepared from toluene-4-sulfonic acid 2-methyl-5-phenyl-2H-pyrazol-3-yl ester and 1-heptyne following the general procedure for the Sonogashira cross-coupling reaction described above. Chromatography eluent: heptane/DCM 1:1; yield (120 mg, 95%); ¹H NMR δ (CDCl₃): 7.78 (d, J=8.20 Hz, 2H), 7.42-7.33 (t, J=8.05 Hz, 2H), 7.32 (m, 1H), 6.62 (s, 1H), 3.93 (s, 3H), 2.48 (t, J=7.25 Hz, 2H), 1.65 (p, J=7.18 Hz, 2H), 1.5-1.32 (m, 4H), 0.94 (t, J=7.22 Hz, 3H); LCMS m/z: 252.

Example 8

5-cyclohex-1-enylethynyl-1methyl-3-phenyl-1H-pyrazole

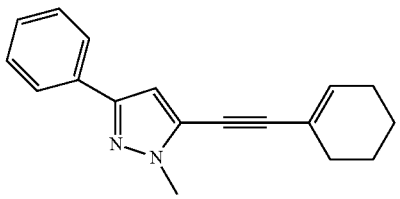 [SMILES: Cn1nc(-c2ccccc2)cc1C#CC1=CCCCC1]

This product was prepared from toluene-4-sulfonic acid 2-methyl-5-phenyl-2H-pyrazol-3-yl ester and 1-ethynyl-cyclohexene following the general procedure for the Sonogashira cross-coupling reaction described above. Chromatography eluent: heptane/DCM 1:1; yield (110 mg, 84%); ¹H NMR δ (CDCl₃): 7.78 (d, J=8.09 Hz, 2H), 7.42-7.33 (t, J=8.11 Hz, 2H), 7.32 (m, 1H), 6.62 (s, 1H), 6.31-6.27 (m, 1H), 3.94 (s, 3H), 2.14-2.22 (m, 4H), 1.58-1.73 (m, 4H); LCMS m/z: 246.

Example 9

1-Methyl-3-phenyl-5-phenylethynyl-1H-pyrazole

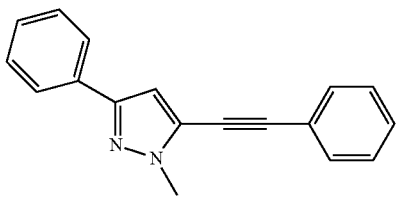 [SMILES: Cn1nc(-c2ccccc2)cc1C#Cc1ccccc1]

This product was prepared from toluene-4-sulfonic acid 2-methyl-5-phenyl-2H-pyrazol-3-yl ester and phenylacetylene. Chromatography eluent: heptane/DCM 1:1; yield (64 mg, 50%); $^1$H NMR δ (CDCl$_3$): 7.78 (d, J=8.22 Hz, 2H), 7.65-7.57 (m 5H), 7.43-7.34 (m, 3H), 6.63 (s, 1H), 3.98 (s, 3H); LCMS m/z: 258.

Example 10

1-Methyl-3-phenyl-5-thiophen-3-ylethynyl-1H-pyrazole

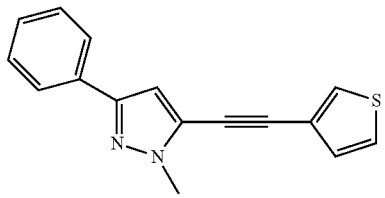 [SMILES: Cn1nc(-c2ccccc2)cc1C#Cc1ccsc1]

This product was prepared from toluene-4-sulfonic acid 2-methyl-5-phenyl-2H-pyrazol-3-yl ester and 3-ethynyl-thiophene following the general procedure for the Sonogashira cross-coupling reaction described above. Chromatography eluent: heptane/EtOAc 95:5; yield (60 mg, 45%); $^1$H NMR δ (CDCl$_3$): 7.78 (d, J=8.10 Hz, 2H), 7.60 (m, 1H), 7.46-7.29 (m, 4H), 7.22 (m, 1H), 6.77 (s, 1H), 4.05 (s, 3H); LCMS m/z: 264.

Example 11

3-(5-Phenyl-pent-1-ynyl)-thiophene-2-carboxylic acid methyl ester

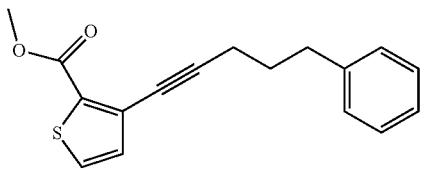 [SMILES: COC(=O)c1sccc1C#CCCCc1ccccc1]

This product was prepared from 3-(toluene-4-sulfonyloxy)-thiophene-2-carboxylic acid methyl ester and pent-4-ynyl-benzene following the general procedure for the Sonogashira cross-coupling reaction described above. Chromatography eluent: heptane/DCM 4:6; yield (114 mg, 80%); $^1$H NMR δ (CDCl$_3$): 7.33 (d, J=4.93 Hz, 1H), 7.16-7.09 (m, 5H), 7.01 (d, J=4.95 Hz, 1H), 3.81 (s, 3H), 2.77 (t, J=7.11 Hz, 2H), 2.42 (t, J=7.16 Hz, 2H), 1.94 (p, J=7.22 Hz, 2H); LCMS m/z: 284.

Example 12

3-Hept-1-ynyl-thiophene-2-carboxylic acid methyl ester

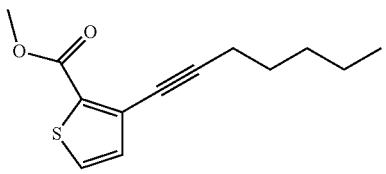 [SMILES: CCCCCC#Cc1ccsc1C(=O)OC]

This product was prepared from 3-(toluene-4-sulfonyloxy)-thiophene-2-carboxylic acid methyl ester and 1-heptyne following the general procedure for the Sonogashira cross-coupling reaction described above. Chromatography eluent: heptane/DCM 1:1; yield (71 mg, 60%); $^1$H NMR δ (CDCl$_3$): 7.32 (d, J=5.03 Hz, 1H), 7.01 (d, J=5.10 Hz, 1H), 3.81 (s, 3H), 2.42 (t, J=7.25 Hz, 2H), 1.57 (p, J=7.19 Hz, 2H), 1.45-1.26 (m, 4H), 0.87 (t, J=7.2 Hz, 3H); LCMS m/z: 236.

Example 13

3-Phenylethynyl-thiophene-2-carboxylic acid methyl ester

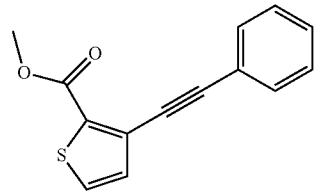 [SMILES: COC(=O)c1sccc1C#Cc1ccccc1]

This product was prepared from 3-(toluene-4-sulfonyloxy)-thiophene-2-carboxylic acid methyl ester and phenylacetylene following the general procedure for the Sonogashira cross-coupling reaction described above. Chromatography eluent: heptane/DCM 1:1; yield (91 mg, 75%); $^1$H NMR δ (CDCl$_3$): 7.53 (m, 2H), 7.39 (d, J=5.02 Hz, 1H), 7.3 (m, 3H), 7.12 (d, J=5.10 Hz, 1H), 3.82 (s, 3H); LCMS m/z: 242.

Example 14

3-(Trifluoromethyl-1-phenylethynyl)-thiophene-2-carboxylic acid methyl ester

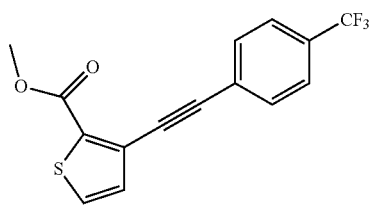 [SMILES: COC(=O)c1sccc1C#Cc1ccc(C(F)(F)F)cc1]

This product was prepared from 3-(toluene-4-sulfonyloxy)-thiophene-2-carboxylic acid methyl ester and 1-ethynyl-4-trifluoromethyl-benzene following the general procedure for the Sonogashira cross-coupling reaction described above. Chromatography eluent: heptane/DCM 1:1; yield (77.5 mg, 50%); $^1$H NMR δ (CDCl$_3$): 7.61 (d, J=8.6 Hz, 2H), 7.53 (d, J=8.61 Hz, 2H), 7.42 (d, J=5.11 Hz, 1H), 7.14 (d, J=5.09 Hz, 1H), 3.84 (s, 3H); LCMS m/z: 310.

Example 15

3-(5-Cyano-pent-1-ynyl)-4-methyl-thiophene-2-carbonitrile

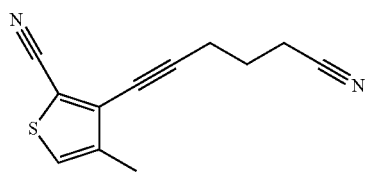

This product was prepared from benzenesulfonic acid 2-cyano-4-methyl-thiophen-3-yl ester and hex-1ynenitrile following the general procedure for the Sonogashira cross-coupling reaction described above. Chromatography eluent: heptane/EtOAc 6:4; yield (53 mg, 50%); $^1$H NMR δ (CDCl$_3$): 6.78 (s, 1H), 2.69 (t, J=7.22 Hz, 2H), 2.58 (t, J=7.24 Hz, 2H), 2.5 (s, 3H), 1.99 (p, J=7.18 Hz, 2H); LCMS m/z: 214.

Example 16

3-(4-Methoxy-phenyl ethynyl)-4-methyl-thiophene-2-carbonitrile

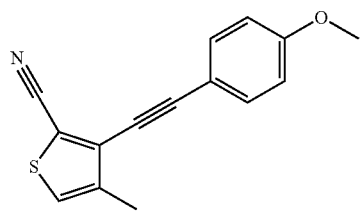 [SMILES: COc1ccc(C#Cc2c(C)csc2C#N)cc1]

This product was prepared from benzenesulfonic acid 2-cyano-4-methyl-thiophen-3-yl ester and 1-ethynyl-4-methoxy-benzene following the general procedure for the Sonogashira cross-coupling reaction described above. Chromatography eluent: heptane/EtOAc 9:1; yield (110 mg, 87%); $^1$H NMR δ (CDCl$_3$): 7.51 (d, J=8.52 Hz, 2H), 6.88 (d, J=8.60 Hz, 2H), 6.81 (s, 1H), 3.84 (s, 3H), 2.51 (s, 3H); LCMS m/z: 253.

Example 17

3-(3-Diethylamino-prop-1-ynyl)-4-methyl-4-thiophene-2-carbonitrile

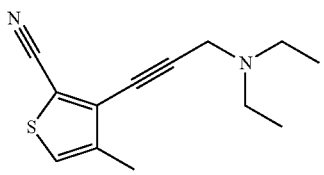 [SMILES: CCN(CC)CC#Cc1c(C)csc1C#N]

This product was prepared from benzenesulfonic acid 2-cyano-4-methyl-thiophen-3-yl ester and diethyl-prop-2-ynyl-amine following the general procedure for the Sonogashira cross-coupling reaction described above. Chromatography eluent: heptane/EtOAc 6:4; yield (73 mg, 63%); $^1$H NMR δ (CDCl$_3$): 6.78 (s, 1H), 3.82 (s, 2H), 2.75 (q, J=7.17 Hz, 4H), 2.51 (s, 3H), 1.22 (t, J=7.14 Hz, 6H); LCMS m/z: 232.

Example 18

1-Benzyl-3-cyclohex-1-enylethynyl-1H-indazole

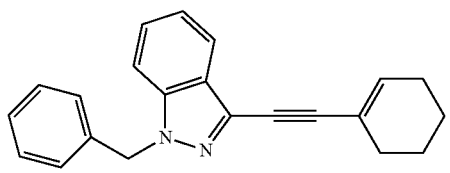 [SMILES: C(#Cc1nn(Cc2ccccc2)c2ccccc12)C1=CCCCC1]

This product was prepared from toluene-4-sulfonic acid 1-benzyl-1H-indazol-3-yl ester and 1-ethynyl-cyclohexene following the general procedure for the Sonogashira cross-coupling reaction described above. Chromatography eluent: heptane/DCM 1:1; yield (81.5, 54%); $^1$H NMR δ (CDCl$_3$): 7.8 (d, J=8.05 Hz, 1H), 7.4-7.19 (m, 8H), 6.37-6.3 (m, 1H), 5.6 (s, 2H), 2.14-2.22 (m, 4H), 1.58-1.73 (m, 4H); LCMS m/z: 312.

Example 19

1-Benzyl-3-hept-1-ynyl-1H-indazole

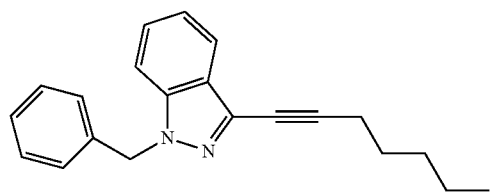 [SMILES: CCCCCC#Cc1nn(Cc2ccccc2)c2ccccc12]

This product was prepared from toluene-4-sulfonic acid 1-benzyl-1H-indazol-3-yl ester and 1-heptyne following the general procedure for the Sonogashira cross-coupling reaction described above. Chromatography eluent: heptane/DCM 1:1; yield (84 mg, 54%); $^1$H NMR δ (CDCl$_3$): 7.9 (d, J=8.02 Hz, 1H), 7.4-7.19 (m, 8H), 5.5 (s, 2H), 2.48 (t, J=7.22 Hz, 2H), 1.65 (p, J=7.18 Hz, 2H), 1.5-1.32 (m, 4H), 0.94 (t, J=7.21 Hz, 3H); LCMS m/z: 302.

Example 20

1-Benzyl-3-(5-phenyl-pent-1-ynyl)-1H-indazole

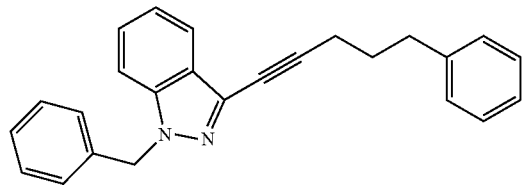 [SMILES: C(#Cc1nn(Cc2ccccc2)c2ccccc12)CCCc1ccccc1]

This product was prepared from toluene-4-sulfonic acid 1-benzyl-1H-indazol-3-yl ester and pent-4-ynyl-benzene following the general procedure for the Sonogashira cross-coupling reaction described above. Chromatography eluent: heptane/DCM 1:1; yield (87.5 mg, 50%); $\delta_H$ (CDCl$_3$): 7.92 (d, J=8.11 Hz, 1H), 7.4-7.19 (m, 8H), 7.15-7.08 (m, 5H), 5.5 (s, 2H), 2.76 (t, J=7.16 Hz, 2H), 2.4 (t, J=7.15 Hz, 2H), 1.91 (p, J=7.21 Hz, 2H); LCMS m/z: 350.

Example 21

1-Benzyl-3-phenylethynyl-1H-indazole

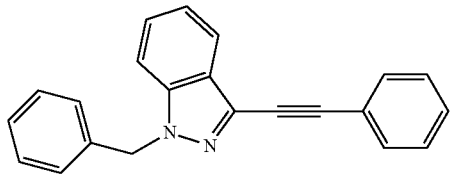 [SMILES: C(#Cc1nn(Cc2ccccc2)c2ccccc12)c1ccccc1]

This product was prepared from toluene-4-sulfonic acid 1-benzyl-1H-indazol-3-yl ester and phenylacetylene following the general procedure for the Sonogashira cross-coupling reaction described above. Chromatography eluent: heptane/DCM 1:1; yield (9.25 mg, 6%); $^1$H NMR δ (CDCl$_3$): 7.92 (d, J=7.92 Hz, 1H), 7.4-7.17 (m, 13H), 5.5 (s, 2H); LCMS m/z: 308.

Example 22

3-Hept-1-ynyl-p-tolyl-1H-pyrazolo[3,4-b]pyridine

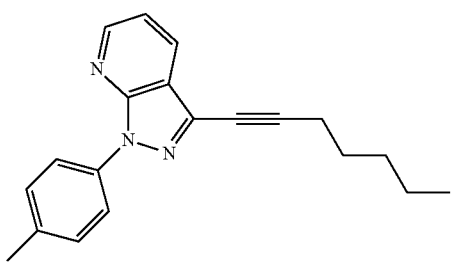 [SMILES: CCCCCC#Cc1nn(-c2ccc(C)cc2)c2ncccc12]

This product was prepared from toluene-4-sulfonic acid 1-p-tolyl-1H-pyrazolo[3,4-b]pyridin-3-yl ester and 1-heptyne following the general procedure for the Sonogashira cross-coupling reaction described above. Chromatography eluent: heptane/iPr$_2$ether 1:1; yield (110 mg, 73%); $^1$H NMR δ (CDCl$_3$): 8.63 (m, 1H), 8.19 (m, 1H), 8.10 (d, J=8.55 Hz, 2H), 7.32 (d, J=8.46 Hz, 2H), 7.20-7.27 (m, 1H), 2.53 (t, J=7.23 Hz, 2H), 2.39 (s, 3H), 1.71 (p, J=7.19 Hz, 2H), 1.57-1.46 (m, 2H), 1.45-1.33 (m, 2H), 0.94 (t, J=7.20 Hz, 3H); LCMS m/z: 303.

Example 23

Diethyl-[3-(1-p-tolyl-1H-pyrazolo[3,4-b]pyridin-3-yl)-prop-2-ynyl]-amine

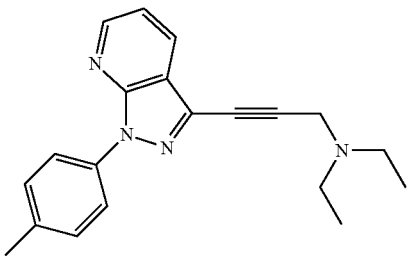 [SMILES: CCN(CC)CC#Cc1nn(-c2ccc(C)cc2)c2ncccc12]

This product was prepared from toluene-4-sulfonic acid 1-p-tolyl-1H-pyrazolo[3,4-b]pyridin-3-yl ester and diethyl-prop-2-ynyl-amine following the general procedure for the Sonogashira cross-coupling reaction described above. Chromatography eluent: heptane/EtOAc 4:6; yield (64 mg, 40%); $^1$H NMR δ (CDCl$_3$): 8.64 (m, 1H), 8.19 (m, 1H), 8.11 (d, J=8.52 Hz, 2H), 7.33 (d, J=8.49 Hz, 2H), 7.21-7.28 (m, 1H), 3.86 (s, 2H), 2.73 (q, J=7.17 Hz, 4H), 2.40 (s, 3H), 1.20 (t, J=7.16 Hz, 6H); LCMS m/z: 318.

Example 24

3-Hept-1-ynyl-pyridine

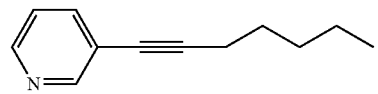

This product was prepared from toluene-4-sulfonic acid pyridin-3-yl ester and 1-heptyne following the general procedure for the Sonogashira cross-coupling reaction described above. Chromatography eluent: heptane/EtOAc 8:2; yield (60 mg, 70%); $^1$H NMR δ (CDCl$_3$): 8.62-8.63 (m, 1H), 8.48-8.46 (m, 1H), 7.68-7.64 (m, 1H), 7.21-7.17 (m, 1H), 2.46 (t, J=7.21 Hz, 2H), 1.63 (p, J=7.15 Hz, 2H), 1.49-1.3 (m, 4H), 0.93 (t, J=7.22 Hz, 3H); LCMS m/z: 173.

Example 25

3-(4-Methoxy-phenyl-1-ethynyl)-pyridine

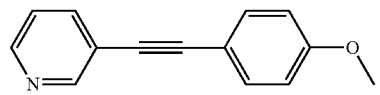

This product was prepared from toluene-4-sulfonic acid pyridin-3-yl ester and 1-ethynyl-4-methoxy-benzene following the general procedure for the Sonogashira cross-coupling reaction described above. Chromatography eluent: heptane/EtOAc 8:2; yield (83 mg, 80%); $^1$H NMR δ (CDCl$_3$): 8.76-

8.74 (m, 1H), 8.50-8.53 (m, 1H), 7.76-7.73 (m, 1H), 7.49-8.46 (m, 2H), 7.24-7.20 (m, 1H), 6.88-6.85 (m, 2H), 3.78 (s, 3H); LCMS m/z: 209.

Example 26

3-(4-Trifluoromethyl-phenylethynyl)-pyridine

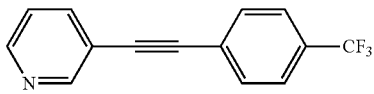 [SMILES: FC(F)(F)c1ccc(C#Cc2cccnc2)cc1]

This product was prepared from toluene-4-sulfonic acid pyridin-3-yl ester and 1-ethynyl-4-trifluoromethyl-benzene following the general procedure for the Sonogashira cross-coupling reaction described above. Chromatography eluent: heptane/EtOAc 8:2; yield (87 mg, 70%); $^1$H NMR δ (CDCl$_3$): 8.75-8.73 (m, 1H), 8.49-8.52 (m, 1H), 7.76-7.73 (m, 1H), 7.49-8.46 (m, 2H), 7.23-7.19 (m, 1H), 6.87-6.84 (m, 2H); LCMS m/z: 247.

Example 27

3-(5-Phenyl-pent-1-ynyl)-pyridine

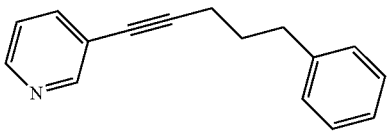 [SMILES: C(#Cc1cccnc1)CCCc1ccccc1]

This product was prepared from toluene-4-sulfonic acid pyridin-3-yl ester and pent-4-ynyl-benzene following the general procedure for the Sonogashira cross-coupling reaction described above. Chromatography eluent: heptane/EtOAc 8:2; yield (80 mg, 72%); $^1$H NMR δ (CDCl$_3$): 8.62-8.63 (m, 1H), 8.48-8.46 (m, 1H), 7.68-7.64 (m, 1H), 7.21-7.17 (m, 6H), 2.76 (t, J=7.11 Hz, 2H), 2.4 (t, J=7.10 Hz, 2H), 1.91 (p, J=7.12 Hz, 2H); LCMS m/z: 221.

Example 28

4-Methyl-6-oct-1-ynyl-pyrimidine

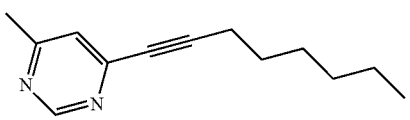

This product was prepared from toluene-4-sulfonic acid 6-methyl-pyrimidin-4-yl ester and 1-octyne following the general procedure for the Sonogashira cross-coupling reaction described above. Chromatography eluent: heptane/EtOAc 8:2; yield (37.6 mg, 40%); $^1$H NMR δ (CDCl$_3$): 9.01 (s, 1H), 7.21 (s, 1H), 2.52 (s, 3H), 2.48 (t, J=7.23 Hz, 2H), 1.63 (p, J=7.17 Hz, 2H), 1.50-1.30 (m, 6H), 0.91 (t, J=7.25 Hz, 3H); LCMS m/z: 188.

Example 29

4-Methyl-6-(5-phenyl-pent-1-ynyl)-pyrimidine

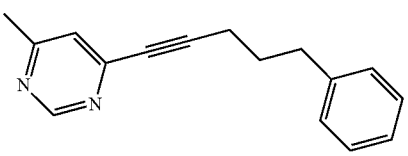 [SMILES: Cc1cc(C#CCCCc2ccccc2)ncn1]

This product was prepared from toluene-4-sulfonic acid 6-methyl-pyrimidin-4-yl ester and pent-4-ynyl-benzene following the general procedure for the Sonogashira cross-coupling reaction described above. Chromatography eluent: heptane/EtOAc 8:2; yield (36.6 mg, 31%); $^1$H NMR δ (CDCl$_3$): 9.01 (s, 1H), 7.31-7.25 (m, 2H), 7.22-7.16 (m, 4H), 2.78 (t, J=7.18 Hz, 2H), 2.51 (s, 3H), 2.41 (t, J=7.17 Hz, 2H), 1.93 (p, J=7.22 Hz, 2H); LCMS m/z: 236.

Example 30

4-(4-Methoxy-phenylethynyl)-6-methyl-pyrimidine

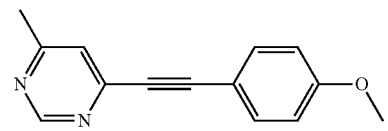

This product was prepared from toluene-4-sulfonic acid 6-methyl-pyrimidin-4-yl ester and 1-ethynyl-4-methoxy-benzene following the general procedure for the Sonogashira cross-coupling reaction described above. Chromatography eluent: heptane/EtOAc 8:2; yield (52 mg, 46%); $^1$H NMR δ (CDCl$_3$): 8.99 (s, 1H), 7.32 (d, J=8.60 Hz, 2H), 7.22 (s, 1H), 7.17 (d, J=8.43 Hz, 2H), 3.83 (s, 3H), 2.51 (s, 3H); LCMS m/z: 224.

Example 31

6-Quinolin-3-yl-hex-5-yn-1-ol

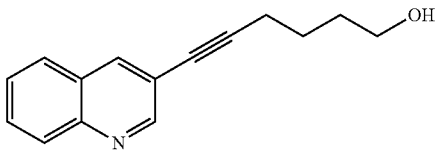 [SMILES: OCCCCC#Cc1cnc2ccccc2c1]

This product was prepared from toluene-4-sulfonic acid quinolin-3-yl ester and hex-5-yn-1-ol following the general procedure for the Sonogashira cross-coupling reaction described above. Chromatography eluent: heptane/EtOAc 6:4; yield (110 mg, 98%); $^1$H NMR δ (CDCl$_3$): 8.89 (s, 1H), 8.21 (s, 1H), 8.11 (d, J=8.62 Hz, 1H), 7.80-7.68 (dm, 2H), 7.62-7.52 (m, 1H), 3.74 (t, J=7.17 Hz, 2H), 2.52 (t, J=7.13 Hz, 2H), 1.83-1.67 (br m, 5H); LCMS m/z: 225.

Example 32

4-Quinolin-3-ylethynyl-phenylamine

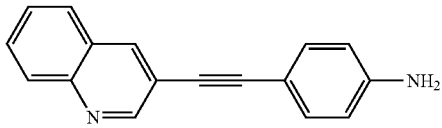

This product was prepared from toluene-4-sulfonic acid quinolin-3-yl ester and 4-ethynyl-phenylamine following the general procedure for the Sonogashira cross-coupling reaction described above. Chromatography eluent: heptane/EtOAc 6:4; yield (120 mg, 98%); $^1$H NMR δ (CDCl$_3$): 8.98 (s, 1H), 8.34 (s, 1H), 8.21 (d, J=8.60 Hz, 1H), 7.87-7.71 (d m, 2H), 7.68-7.57 (m, 1H), 7.40 (d, J=8.36 Hz, 2H), 6.67 (d, J=8.38 Hz, 2H), 4.46 (br s, 2H); LCMS m/z: 244.

What is claimed is:
1. A process for preparing a compound of formula I

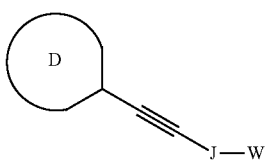

(I)

and/or all stereoisomeric forms of the compound of formula I, and/or mixtures of these forms in any ratio, and/or a physiologically tolerated salt of the compound of formula I, wherein
D is a (C$_4$-C$_{14}$)-heteroaryl ring system, which is a 4- to 14-membered aromatic cyclic residue, which consists depending on the number of ring atoms out of one, two or three ring systems, wherein one or more of the 4 to 14 ring carbon atoms are replaced by heteroatoms chosen from nitrogen, oxygen or sulfur, wherein heteroaryl is unsubstituted or mono-, di-, tri- four- or five times substituted independently of one another by R1,
J is a covalent bond,
—(C$_1$-C$_6$)-alkylene, wherein alkylene is unsubstituted or mono-, di- or trisubstituted independently of one another by R2,
—(C$_3$-C$_8$)-cycloalkyl, wherein cycloalkyl is unsubstituted or mono-, di- or trisubstituted independently of one another by R14,
—(C$_6$-C$_{14}$)-aryl, wherein aryl is unsubstituted or mono-, di-, tri- or four times substituted independently of one another by R13, or
—(C$_4$-C$_{14}$)-heteroaryl ring system, which is as defined above, wherein heteroaryl is unsubstituted or mono-, di-, tri- or four times substituted independently of one another by R13,
W is hydrogen atom,
—(C$_1$-C$_6$)-alkyl, wherein alkyl is unsubstituted or mono-, di- or trisubstituted independently of one another by R2,
—(C$_3$-C$_8$)-cycloalkyl, wherein cycloalkyl is unsubstituted or mono-, di- or trisubstituted independently of one another by R2,
—(C$_6$-C$_{14}$)-aryl, wherein aryl is unsubstituted or mono-, di-, tri- or four times substituted independently of one another by R2, or
—(C$_4$-C$_{14}$)-heteroaryl ring system, which is as defined above, wherein heteroaryl is unsubstituted or mono-, di-, tri- or four times substituted independently of one another by R2,
R1 and R2 are independent of one another identical or different and are
a) hydrogen atom,
b) —(C$_1$-C$_4$)-alkyl, wherein alkyl is unsubstituted or substituted one, two or three times by R13,
c) halogen,
d) phenyloxy-, wherein phenyloxy is unsubstituted or substituted one, two or three times by R13,
e) —(C$_1$-C$_3$)-fluoroalkyl,
f) —N(R10)-(C$_1$-C$_4$)-alkyl, wherein alkyl is unsubstituted or substituted one, two or three times by R13,
g) —(C$_6$-C$_{14}$)-aryl, wherein aryl is unsubstituted or mono-, tri- or four times substituted independently of one another by R13,
h) —(C$_4$-C$_{14}$)-heteroaryl ring system, which is as defined above, wherein heteroaryl is unsubstituted or mono-, di-, tri- or four times substituted independently of one another by R13,
i) —(C$_3$-C$_8$)-cycloalkyl, wherein said cycloalkyl is unsubstituted or mono-, di-, tri- or four times substituted independently of one another by R13,
j) a 3- to 7-membered cyclic residue, containing 1, 2, 3 or 4 heteroatoms chosen from nitrogen, sulfur or oxygen, wherein said cyclic residue is unsubstituted or mono-, di-, tri- or four times substituted independently of one another by R13,
k) —O—CF$_3$,
l) —O—(C$_1$-C$_4$)-alkyl, wherein alkyl is unsubstituted or substituted one to three times by R13,
m) —NO$_2$,
n) —CN,
o) —OH,
p) —C(O)—R10,
q) —C(O)—O—R11,
r) —C(O)—N(R11)-R12,
s) —N(R11)-R12,
t) —N(R10)-SO$_2$—R10,
v) —S—R10,
w) —SO$_n$—R10, wherein n is 1 or 2,
x) —SO$_2$—N(R11)-R12 or
y) —Si(R11)(R11)-R12,
R10 is hydrogen atom, —(C$_1$-C$_3$)-fluoroalkyl or —(C$_1$-C$_6$)-alkyl,
R11 and R12 are independently of one another identical or different and are
a) hydrogen atom,
b) —(C$_1$-C$_6$)-alkyl, wherein alkyl is unsubstituted or mono-, di- or trisubstituted independently of one another by R13,
c) —(C$_6$-C$_{14}$)-aryl-, wherein aryl is unsubstituted or mono-, di- or trisubstituted independently of one another by R13,
d) —(C$_4$-C$_{14}$)-heteroaryl ring system, which is as defined above, wherein heteroaryl is unsubstituted or mono-, di- or trisubstituted independently of one another by R13,
R13 is halogen, —NO$_2$, —CN, =O, —OH, —(C$_1$-C$_8$)-alkyl, —(C$_1$-C$_8$)-alkoxy, —CF$_3$, phenyloxy-, —C(O)—

R10, —C(O)—O—R17, —C(O)—N(R17)-R18, —S—R10, —N(R17)-R18, —N(R10)-SO$_2$—R10, —SO$_n$—R10, wherein n is 1 or 2, —SO$_2$—N(R17)-R18, —(C$_6$-C$_{14}$)-aryl, wherein aryl is unsubstituted or mono-, di- or trisubstituted independently of one another by R14, —(C$_4$-C$_{14}$)-heteroaryl ring system, which is as defined above, wherein heteroaryl is unsubstituted or mono-, di- or trisubstituted independently of one another by R14, —(C$_3$-C$_8$)-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, R14 is halogen, —OH, =O, —CN, —CF$_3$, —(C$_1$-C$_8$)-alkyl, —(C$_1$-C$_4$)-alkoxy, —NO$_2$, —C(O)—OH, —NH$_2$, —C(O)—O—(C$_1$-C$_4$)-alkyl, —(C$_1$-C$_8$)-alkylsulfonyl, —C(O)—NH—(C$_1$-C$_8$)-alkyl, —C(O)—N—[(C$_1$-C$_8$)-alkyl]$_2$, —C(O)—NH$_2$—S—R10, —N(R10)-C(O)—NH—(C$_1$-C$_8$)-alkyl, or —N(R10)-C(O)—N—[(C$_1$-C$_8$)-alkyl]$_2$, R17 and R18 are independently of one another identical or different and are a) hydrogen atom, b) —(C$_1$-C$_6$)-alkyl, c) —(C$_6$-C$_{14}$)-aryl- or d) —(C$_4$-C$_{14}$)-heteroaryl ring, system, which is as defined above, said process comprises reacting a compound of formula II

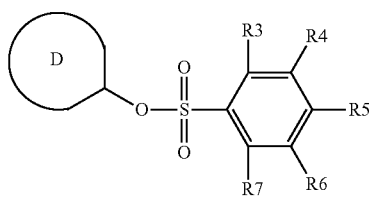

(II)

wherein D is as defined in formula I and

R3, R4, R5, R6 and R7 are independently of one another identical or different and are a) hydrogen atom, b) —(C$_1$-C$_4$)-alkyl, c) halogen, d) —(C$_1$-C$_3$)-fluoroalkyl, e) —O—CF$_3$, f) —NO$_2$, g) —CN, h) —OH, i) —C(O)—R10, j) —C(O)—O—R11, k) —C(O)—N(R11)-R12, l) —N(R11)-R12, m) —SO$_n$—R10, wherein n is 1 or 2, or n) —SO$_2$—N(R11)-R12, with a compound of formula III

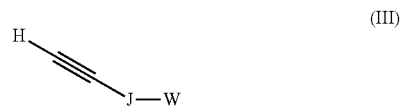

(III)

wherein J and W are as defined in formula I,
in the presence of a palladium catalyst, a base, a ligand and a probe solvent to give a compound of formula I and
optionally the compound of formula I is converted to its physiologically tolerated salt.

2. The process according to claim 1, wherein a compound of formula I is prepared, wherein D is a (C$_4$-C$_{14}$)-heteroaryl ring system, wherein heteroaryl is selected from acridinyl, azaindole (1H-pyrrolo-pyridinyl), azabenzimidazolyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, chromanyl, chromenyl, furanyl, furazanyl, imidazolyl, indanyl, 1H-indazolyl, indolizinyl, indolyl, 3H-indolyl, isobenzofuranyl, isoindazolyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, 1,4-oxazepinyl, oxazolyl, phenanthridinyl, phenazinyl, phenothiazinyl, phenoxazinyl, phthalazinyl, pteridinyl, purinyl, pyrazinyl, pyrazolo[3,4-b]pyridine, pyrazolyl, pyridazinyl, pyridooxazolyl, pyridoimidazolyl, pyridothiazolyl, pyridinyl, pyridyl, pyrimidinyl, 2H-pyrrolyl, pyrrolyl, quinolinyl, 4H-quinolizinyl, quinoxalinyl, quinuclidinyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, 1,2-thiazinyl, 1,3-thiazinyl, 1,4-thiazinyl, 1,3-thiazolyl, thiazolyl, thienyl, thienothiazolyl, thienooxazolyl, thienoimidazolyl, thiophenolyl, thiophenyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl and wherein heteroaryl is unsubstituted or depending on the number of atoms is mono-, di-, tri- four- or five times substituted independently of one another by R1;

J is a covalent bond,
—(C$_1$-C$_6$)-alkylene, wherein alkylene is unsubstituted or mono-, di- or trisubstituted independently of one another by R2,
—(C$_3$-C$_6$)-cycloalkyl, wherein cycloalkyl is unsubstituted or mono-, di- or trisubstituted independently of one another by R14,
phenyl, wherein phenyl is unsubstituted or mono-, di-, tri- or four times substituted independently of one another by R13, or
—C$_4$-C$_{14}$-heteroaryl, wherein heteroaryl is as defined above and is unsubstituted or mono-, di-, tri- or four times substituted independently of one another by R13, W is hydrogen atom,
—(C$_1$-C$_6$)-alkyl, wherein alkyl is unsubstituted or mono-, di- or trisubstituted independently of one another by R2,
—(C$_3$-C$_6$)-cycloalkyl, wherein cycloalkyl is unsubstituted or mono-, di- or trisubstituted independently of one another by R2, phenyl, wherein phenyl is unsubstituted or mono-, di-, tri- or four times substituted independently of one another by R2, or —($C_4$-$C_{14}$)-heteroaryl, wherein heteroaryl is as defined above and is unsubstituted or mono-, di-, tri- or four times substituted independently of one another by R2;

R1 and R2, are independent of one another identical or different and are a) hydrogen atom,
b) F,
c) Cl,
d) —($C_1$-$C_4$)-alkyl, wherein alkyl is unsubstituted or substituted one to three times by R13,
e) —($C_1$-$C_3$)-fluoroalkyl,
f) phenyl, wherein phenyl is unsubstituted or substituted one to three times by R13,
g) —($C_4$-$C_{14}$)-heteroaryl, wherein heteroaryl is as defined above and is unsubstituted or mono-, di-, tri- or four times substituted independently of one another by R13,
h) —($C_3$-$C_8$)-cycloalkyl, wherein said cycloalkyl is unsubstituted or mono-, di-, tri- or four times substituted independently of one another by R13,
i) a 3- to 7-membered cyclic residue, wherein the cyclic residue is selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole and 1,2,4-triazole, and wherein said cyclic residue is unsubstituted or mono-, di-, tri- or four times substituted independently of one another by R13,
j) —O—$CF_3$,
k) —O—($C_1$-$C_4$)-alkyl, wherein alkyl is unsubstituted or substituted one to three times by R13,
l) —N(R10)-($C_1$-$C_4$)-alkyl, wherein alkyl is unsubstituted or substituted one to three times by R13,
m) —CN,
n) —OH,
o) phenyloxy-, wherein phenyloxy is unsubstituted or substituted one to three times by R13,
p) —C(O)—O—R11,
q) —C(O)—N—(R11)-R12,
r) —N(R11)-R12,
s) —N(R10)-$SO_2$—R10,
t) —S—R10,
v) —$SO_n$—R10, wherein n is 1 or 2,
w) —$SO_2$—N(R11)-R12,
x) —C(O)—R10,
y) —Si(R11)(R11)-R12, R10 is hydrogen atom, —($C_1$-$C_3$)-fluoroalkyl or —($C_1$-$C_6$)-alkyl, R11 and R12 are independently of one another identical or different and are a) hydrogen atom,
b) $C_1$-$C_4$)-alkyl, wherein alkyl is =substituted or mono-, di- or trisubstituted independently of one another by R13,
c) phenyl, wherein phenyl is unsubstituted or mono-, di- or trisubstituted independently of one another by R13, or
d) —($C_4$-$C_{14}$)-heteroaryl, wherein heteroaryl is as defined above and is unsubstituted Or mono-, di- or trisubstituted independently of one another by R13, R13 is F, Cl, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N(R17)-R18, —N(R17)-R18, —S—R10, —N(R10)-$SO_2$—R10, —$SO_n$—R10, wherein n is 1 or 2, —$SO_2$—N(R17)-R18, phenyl, wherein phenyl is unsubstituted or mono-, di- or trisubstituted independently of one another by R14, —($C_4$-$C_{14}$)-heteroaryl, wherein heteroaryl is as defined above and is unsubstituted or mono-, di- or trisubstituted independently of one another by R14, —($C_3$-$C_6$)-cycloalkyl, wherein said cycloalkyl is unsubstituted or mono-, di- or trisubstituted independently of one another by R14, or a 3- to 7-membered cyclic residue, wherein said cyclic residue is as defined above and is unsubstituted or mono-, di- or trisubstituted independently of one another by R14, R14 is F, Cl, —OH, =O, —CN, —$CF_3$, —($C_1$-$C_8$)-alkyl, —($C_1$-$C_4$)-alkoxy, —C(O)—OH, —$NH_2$, —C(O)—O—($C_1$-$C_4$)-alkyl, —($C_1$-$C_8$)-alkylsulfonyl, —C(O)—$NH_2$, —C(O)—NH—($C_1$-$C_8$)-alkyl, —C(O)—N—[($C_1$-$C_8$)-alkyl]$_2$, —S—R10, —N(R10)-C(O)—NH—($C_1$-$C_8$)-alkyl or —N(R10)-C(O)—N—[($C_1$-$C_8$)-alkyl]$_2$, R17 and R18 are independently of one another identical or different and are a) hydrogen atom,
b) —($C_1$-$C_4$)-alkyl,
c) phenyl or
d) —($C_4$-$C_{14}$)-heteroaryl, wherein heteroaryl is as defined above, and R3, R4, R5, R6 and R7 are independently of one another identical or different and are a) hydrogen atom,
b) —($C_1$-$C_4$)-alkyl,
c) halogen,
d) —($C_1$-$C_3$)-fluoroalkyl,
e) —O—$CF_3$,
f) —$NO_2$
g) —CN,
h) —OH,
i) —C(O)—R10,
j) —C(O)—O—R11,
k) —C(O)—N(R11)-R12,
l) —N(R11)-R12,
m) —$SO_n$R10, wherein n is 1 or 2, or
n) —$SO_2$—N(R11)-R12.

3. The process according to claim 1, wherein a compound of formula I is prepared, wherein D is a ($C_4$-$C_{14}$)-heteroaryl ring system, wherein heteroaryl is selected from 1H-indazolyl, pyrazolyl, pyridyl, pyrimidinyl, quinolinyl and thienyl, and wherein heteroaryl is unsubstituted or is mono- or disubstituted independently of one another by R1;

J is a covalent bond, —($C_1$-$C_4$)-alkylene, cyclohexenyl, cyclohexyl, phenyl, wherein phenyl is unsubstituted or mono- or disubstituted independently of one another by R13, or thienyl, W is hydrogen atom, —(C$_1$-C$_4$)-alkyl, cyclohexenyl, cyclohexyl, phenyl, wherein phenyl is unsubstituted or mono- or disubstituted independently of one another by R2, or thienyl, R1 and R2, are independent of one another identical or different and are
a) hydrogen atom,
b) F,
c) Cl,
d) (C$_1$-C$_4$)-alkyl, wherein alkyl is substituted or substituted one time by R13,
e) —(C$_1$-C$_3$)-fluoroalkyl,
f) phenyl; wherein phenyl is unsubstituted or substituted one or two times by R13,
g) —O—(C$_1$-C$_4$)-alkyl wherein alkyl is unsubstituted or substituted one or two times by R13,
h) —N(R10)-(C$_1$-C$_4$)-alkyl, wherein alkyl is unsubstituted or substituted one or two times by R13,
i) —CN,
j) —OH,
k) —C(O)—O—R11 or
l) —N(R11)$_7$R12, R10 is hydrogen atom or —(C$_1$-C$_4$)-alkyl,
R11 and R12 are independently of one another identical or different and are hydrogen atom or —(C$_1$-C$_4$)-alkyl,
R13 is F, Cl, —CN, —OH, —(C$_1$-C$_4$)-alkyl, —CF$_3$, phenyl or —N(R17)-R18,
R17 and R18 are independently of one another identical or different and are hydrogen atom or —(C$_1$-C$_4$)-alkyl, and
R3, R4, R5, R6 and R7 are independently of one another identical or different and are hydrogen atom or —(C$_1$-C$_4$)-alkyl.

4. The process according to claim 1, wherein one of the following compounds of formula I is prepared:
1-Methyl-3-(5-phenyl-pent-1-ynyl)-5-trifluoromethyl-1H-pyrazole, 3-Hept-1-ynyl-1-methyl-5-trifluoromethyl-1H-pyrazole, 3-cyclohex-1-enylethynyl-1-methyl-5-trifluoromethyl-1H-pyrazole, 1-Methyl-3-phenylethynyl-5-trifluoromethyl-1H-pyrazole, 1-Methyl-3-phenyl-5-(5-phenyl-pent-1-ynyl)-1H-pyrazol-3-ylethynyl)-phenylamine, 1-Methyl-3-phenyl-5-(5-phenyl-pent-1-ynyl)-1H-pyrazole, 5-hept-1-ynyl-1-methyl-3-phenyl-1H-pyrazole, 5-cyclohex-1-enylethynyl-1methyl-3-phenyl-1H-pyrazole, 1-Methyl-3-phenyl-5-phenylethynyl-1H-pyrazole, 1-Methyl-3-phenyl-5-thiophen-3-ylethynyl-1H-pyrazole, 3-(5-Phenyl-pent-1-ynyl)-thiophene-2-carboxylic acid methyl ester, 3-Hept-1-ynyl-thiophene-2-carboxylic acid methyl ester, 3-Phenylethynyl-thiophene-2-carboxylic acid methyl ester, 3-(Trifluoro-methyl-1-phenylethynyl)-thiophene-2-carboxylic acid methyl ester, 3-(5-Cyano-pent-1-ynyl)-4-methyl-thiophene-2-carbonitrile, 3-(4-Methoxy-phenyl ethynyl)-4-methyl-thiophene-2-carbonitrile, 3-(3-Diethylamino-prop-1-ynyl)-4-methyl-4-thiophene-2-carbonitrile, 1-Benzyl-3-cyclohex-1-enylethynyl-1H-indazole, 1-Benzyl-3-hept-1-ynyl-1H-indazole, 1-Benzyl-3-(5-phenyl-pent-1-ynyl)-1H-indazole, 1-Benzyl-3-phenylethynyl-1H-indazole, 3-Hept-1-ynyl-p-tolyl-1H-pyrazolo[3,4-b]pyridine, Diethyl-[3-(1-p-tolyl-H-pyrazolo[3,4-b]pyridin-3-yl)-prop-2-ynyl]-amine, 3-Hept-1-ynyl-pyridine, 3-(4-Methoxy-phenyl-1-ethynyl)-pyridine, 3-(4-Trifluoromethyl-phenylethynyl)-pyridine, 3-(5-Phenyl-pent-1-ynyl)-pyridine, 4-Methyl-6-oct-1-ynyl-pyrimidine, 4-Methyl-6-(5-phenyl-pent-1-ynyl)-pyrimidine, 4-(4-Methoxy-phenylethynyl)-6-methyl-pyrimidine, 6-Quinolin-3-yl-hex-5-yn-1-ol or 4-Quinolin-3-ylethynyl-phenylamine.

5. The process according to claim 1, wherein the palladium catalyst is selected from: Pd-alkanoates, Pd-alkanoate complexes, Pd-acetonates, Pd-halides, Pd-halide complexes and Pd-phosphine complexes, provided that the catalyst contains no monophosphino-biphenyl derivative as a ligand.

6. The process according to claim 5, wherein the palladium catalyst is selected from: palladium (II) acetate, palladium (II) trifluoroacetate, palladium (II) hexafluoroacetylacetonate, palladium (II) bromide, palladium (II) chloride, palladium (II) iodide, palladium (II) nitrate, palladium (II) acetylacetonate, dichloro-bis-acetonitrile palladium (II), tetrakis(triphenylphosphine)palladium (0), trans-di(μ-acetato)bis[o-(di-o-tolylphosphino)benzyl]dipalladium (II), tris(dibenzylideneacetone)dipalladium(0), tris(dibenzylideneacetone)dipalladium(0) chloroform adduct, palladium (II) chloride, 2,2'-bis(diphenylphosphino)-1,1'-binaphthylpalladium(II) chloride, acetato(2'-di-tert-butylphosphino-1,1'-biphenyl-2-yl)palladium(II), (1,2-Bis(diphenylphosphino)ethane)dichloropalladium(II), Bis[1,2-bis(diphenylphosphino)ethane]palladium (0), [(2S,3S)-Bis(diphenylphosphino)-butane][eta3-allyl]palladium(II) perchlorate, 1,3-bis(2,4,6-trimethylphenyl)i-midazol-2-ylidene(1,4-naphthoquinone) palladium (0) dimer, [P,P'-1,3-bis(di-i-propylphosphino)propane][P-1,3-bis(di-1-propylphosphino)propane] palladium (0), 2-(dimethylamino)ferrocen-1-yl-palladium (II) chloride dinorbornylphosphine complex, chloro(di-2-norbornylphosphino)(2-dimethylaminomethylferrocen-1-yl)palladim (II), 1,1'-bis(diphenylphosphino)ferrocene palladium (II) chloride, dichloro[1,1'-bis(diphenylphosphino)ferrocene]palladium (II) dichloromethane adduct, dichloro((S)—N,N-dimethyl-1-((R)-2-(diphenylphosphino)ferrocenyl)-ethylamine)palladium, (1,1'-bis(diphenylphosphino)ferrocene)palladium(II) chloride, [(2S)-1-[(1S)-1-[bis(1,1-dimethylethyl)phosphino-kappaP]ethyl]-2-(diphenylphosphino-kappaP)ferrocene]palladium dichloride, [(2S)-1-[(1S)-1-[bis(1,1-dimethylethyl)phosphino-kappaP]ethyl]-2-(diphenylphosphino-kappaP)ferrocene][tris(2-methylphenyl)phosphine]palladium, [(2R)-1-[(1R)-1-[bis(1,1-dimethylethyl)phosphino-kappaP]ethyl]-2-(dicyclohexylphosphino-kappaP)ferrocene][tris(2-methylphenyl)phosphine]palladium.

7. The process according to claim 5, wherein the palladium catalyst is palladium (II) acetate, dichloro-bis-acetonitrile palladium (II), palladium (II) bromide, palladium (II) iodide, palladium (II) acetate, palladium (II) trifluoroacetate, tris(dibenzylideneacetone)dipalladium(0), palladium (II) chloride1-[1-[bis(1,1-dimethylethyl)phosphino-kappaP]ethyl]-2-(diphenylphosphino-kappaP)ferrocene]palladium dichloride, 1-[1-[bis(1,1-dimethylethyl)phosphino-kappa)]ethyl]-2-(diphenylphosphino-kappaP)ferrocene][tris(2-methylphenyl)phosphine]palladium, [1-[(1-[bis(1,1-dimethylethyl)phosphino-kappaP]ethyl]-2-(dicyclohexylphosphino-kappaP)ferrocene][tris(2-methylphenyl)phosphine] palladium, or palladium (II) trifluoroacetate.

8. The process according to claim 1, wherein the base is selected out of the group of carbonates, phosphates, fluorides, alkoxides and hydroxides with a suitable metal as counterion.

9. The process according to claim 8, wherein the base is selected out of the group: potassium carbonate, potassium phosphate and caesium carbonate.

10. The process according to claim 1, wherein the ligand is selected out of the group, provided that the phosphine ligand is not a monophosphino-biphenyl derivative: (+/−)-2,2'-bis(diphenylphosphino)-1,1'-binaphthalene, (9,9-dimethyl-9h-xanthene-4,5-diyl)bis[diphenyl phosphine], (R)-(−)-1-[(S)-

2-(diphenylphosphino) ferrocenyl]ethyldicyclohexylphosphine, 1,2-Bis(diphenylphosphino)ethane, (2S,3S)-(−)-bis(diphenylphosphino)butane, 1,3-Bis(diphenylphosphino)propane, (R)-(−)-1-[(S)-2-(Dicyclohexylphosphino)ferrocenyl]-ethyldi-tert-butylphosphine, (R)-(+)-1,1'-Bis(diphenylphosphino)-2,2'-bis(N,N-diisopropylamido)ferrocene, (S,S)-1-[1-(Di-tert-butylphosphino)ethyl]-2-(diphenylphosphino)ferrocene, (1R,2R)-(+)-1,2-Diaminocyclohexane-N,N'-bis(2-diphenylphosphino-1-naphtoyl, (−)-1,2-Bis[(2S,5S)-2,5-diisopropylpholano)-benzene, Bis[(2-diphenylphosphino)phenyl]ether, (S)-(−)-2,2'-Bis(di-para-tolylphosphino)-1,1'-binaphyl, 4,5-Bis(bis(3,5-bis(trifluoromethyl)phenyl)phosphino)-9,9-dimethylxanthen, (R)-(−)-1-[(S)-2-(di(3,5-bis-trifluoromethylphenyl)phosphino)-ferrocenyl]ethyldicyclohexylphosphine, (R)-(−)-1-[(S)-2-(di(3,5-bis-trifluoromethylphenyl)phosphino)ferrocenyl]ethyldi(3,5-dimethylphenyl)-phosphine, 2,2'-bis[(2',4',6'-triisopropyl)dicyclohexylphosphino]-biphenyl, 2,2'-bis(di-tert-butylphosphino)biphenyl, (R)-(+)-1-[(R)-2-(2'-di(3,5-xylyl)phosphino-phenyl)ferrocenyl]ethyldi(3,5-xylyl9phosphine, (R)-(−)-1-[(S)-2-(bis(3,5-dimethyl-4-methoxyphenyl)phosphino)ferrocenyl]ethyldicyclohexylphosphine, (R)-(+)-1-[(R)-2-(2'-di(3,5-dimethyl-4-methoxyphenyl)phosphinophenyl)-ferrocenyl]ethyldi(bis-3,5-trifluoromethylphenyl)phosphine, (R)-(−)-1-[(S)-2-(dicyclohexylphosphino)ferrocenyl]ethyldi-t-butylphosphine, (R)-(−)-1-[(S)-2-bis(4-trifluoromethylphenyl)phosphino)ferrocenyl]ethyl-di-t-butylphosphine, (1,1'-ferrocenediyl)phenylphosphine, (R)-(+)-1,1'-bis(diphenylphosphino)-2,2'-bis(N,N-diisopropylamido)ferrocene, 1,2,3,4,5-pentaphenyl-1'-(di-t-butylphosphino)ferrocene, (S)-(+)-1-[(R)-2-(diphenylphosphino)ferrocenyl]ethyldi-t-butylphosphine, (R)-(−)-1-[(S)-2-(diphenylphosphino)ferrocenyl]ethyldi-t-butylphosphine, (S)-(+)-1-[(R)-2-(dicyclohexylphosphino)ferrocenyl]ethyldiphenylphosphine, 1,1'-bis(di-i-propylphosphino)ferrocene, (R)-(−)-1-[(S)-2-(dicyclohexylphosphino)-ferrocenyl]ethyldiphenylphosphine, (S)-(+)-1-[(R)-2-(dicyclohexylphosphino)ferrocenyl]ethyldicyclohexylphosphine, (R)-(−)-1-[(S)-2-(dicyclohexyl-phosphino) ferrocenyl]ethyldicyclohexylphosphine, (R)-(−)-1-[(S)-2-(diphenylphosphino) ferrocenyl]ethyldicyclohexylphosphine, 1,1'-bis(di-tert-butylphosphino)ferrocene, (−)-(R)-1-((S)-2-(diphenylphosphino) ferrocenyl)ethyl methyl ether, (+)(S)-1-((R)-2-(diphenylphosphino)ferrocenyl)ethyl methyl ether, (+)-(S)—N,N-dimethyl-1-((R)-1',2-bis(diphenylphosphino)-ferrocenyl)ethylamine, (+)-(S)—N,N-dimethyl-1-((R)-2-(diphenylphosphino)-ferrocenyl)ethylamine, 1,1'-bis(diphenylphosphino)ferrocene, tri-tert-butylphosphine, di-tert-butylmethylphosphonium tetrafluoroborate, tri-2-furylphosphine.

11. The process according to claim 10, wherein the ligand is selected out of the group: 1-[2-(dicyclohexylphosphino)ferrocenyl]ethyldi-t-butylphosphine or 1-[2-(diphenylphosphino)ferrocenyl]ethyldi-t-butylphosphine.

12. The process according to claim 1, wherein the protic solvent is selected out of the group: water, methanol, ethanol, trifluoroethanol, n-propanol, i-propanol, n-butanol, butanol, t-butanol, n-pentanol, i-pentanol, 2-methyl-2-butanol, 2-trifluoromethyl-2-propanol, 2,3-dimethyl-2-butanol,3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol,3-hexanol, cyclopropylmethanol, cyclopropanol, cyclobutanol, cyclopentanol and cyclohexanol.

13. The process according to claim 12, wherein the protic solvent is selected out of the group: i-butanol, t-butanol, 2-methylbutan-2-ol, 3-methyl-3-pentanol and 3-ethyl-3-pentanol.

14. The process according to claim 1, wherein the reaction between the compound of formula II and formula III is carried out in the temperature range from 60° C. to 150° C.

15. The process according to claim 14, wherein the reaction between the compound of formula II and formula III is carried out in the temperature range from 70° C. to 100° C.

* * * * *